United States Patent
Mallick

(10) Patent No.: US 11,448,647 B2
(45) Date of Patent: Sep. 20, 2022

(54) METHODS OF ASSAYING PROTEINS

(71) Applicant: NAUTILUS BIOTECHNOLOGY, INC., Seattle, WA (US)

(72) Inventor: Parag Mallick, San Mateo, CA (US)

(73) Assignee: NAUTILUS BIOTECHNOLOGY, INC., Seattle, WA (US)

( * ) Notice: Subject to any disclaimer, the term of this patent is extended or adjusted under 35 U.S.C. 154(b) by 0 days.

(21) Appl. No.: 17/534,405

(22) Filed: Nov. 23, 2021

(65) Prior Publication Data
US 2022/0074931 A1 Mar. 10, 2022

Related U.S. Application Data

(63) Continuation of application No. 17/191,632, filed on Mar. 3, 2021, which is a continuation of application No. 17/153,877, filed on Jan. 20, 2021, which is a continuation of application No. 16/659,132, filed on Oct. 21, 2019, now Pat. No. 10,948,488, which is a continuation of application No. 16/426,917, filed on May 30, 2019, now Pat. No. 10,473,654, which is a
(Continued)

(51) Int. Cl.
*G01N 33/543* (2006.01)
*C12Q 1/6804* (2018.01)

(52) U.S. Cl.
CPC ..... *G01N 33/54353* (2013.01); *C12Q 1/6804* (2013.01); *G01N 2458/10* (2013.01)

(58) Field of Classification Search
CPC ......... G01N 33/54333; G01N 2458/10; C12Q 1/6804
See application file for complete search history.

(56) References Cited

U.S. PATENT DOCUMENTS 5,445,934 A 8/1995 Fodor et al.
5,849,878 A 12/1998 Cantor et al.
(Continued)

FOREIGN PATENT DOCUMENTS

CN 100500865 C 6/2009
EP 2872898 B1 12/2016
(Continued)

OTHER PUBLICATIONS

3-Aminopropyl)triethoxysilane. Wikipedia.org. Apr. 5, 2019 (Apr. 5, 2019), entire document esp p. 1 (https://en.wikipedia.org/w/index.php?title=(3-Aminopropyl)triethoxysilane&oldid=891131780).
(Continued)

*Primary Examiner* — Jeremy C Flinders
(74) *Attorney, Agent, or Firm* — Knobbe, Martens, Olson & Bear LLP

(57) ABSTRACT

Methods and systems for identifying a protein within a sample are provided herein. A panel of antibodies are acquired, none of which are specific for a single protein or family of proteins. Additionally, the binding properties of the antibodies in the panel are determined. Further, the protein is iteratively exposed to a panel of antibodies. Additionally, a set of antibodies which bind the protein are determined. The identity of the protein is determined using one or more deconvolution methods based on the known binding properties of the antibodies to match the set of antibodies to a sequence of a protein.

24 Claims, 19 Drawing Sheets

Specification includes a Sequence Listing.

Related U.S. Application Data continuation of application No. PCT/US2017/064322, filed on Dec. 1, 2017.

(60) Provisional application No. 62/500,455, filed on May 2, 2017, provisional application No. 62/429,063, filed on Dec. 1, 2016.

(56) References Cited

U.S. PATENT DOCUMENTS

| | | | |
|---|---|---|---|
| 6,720,595 | B2 | 4/2004 | Clevenger et al. |
| 6,998,241 | B2 | 2/2006 | Boga |
| 7,252,954 | B2 | 8/2007 | Wang et al. |
| 7,842,793 | B2 | 11/2010 | Rothemund |
| 7,932,060 | B2 | 4/2011 | Nadeau et al. |
| 8,501,923 | B2 | 8/2013 | Rothemund |
| 9,340,416 | B2 | 5/2016 | Maune et al. |
| 9,528,984 | B2 | 12/2016 | Mitra |
| 9,880,175 | B2 | 1/2018 | Mitra |
| 10,175,248 | B2 | 1/2019 | Mitra |
| 10,351,909 | B2 | 7/2019 | Drmanac et al. |
| 10,473,654 | B1 | 11/2019 | Mallick |
| 10,571,473 | B2 | 2/2020 | Mitra |
| 10,741,382 | B2 | 8/2020 | Sills et al. |
| 10,829,816 | B2 | 11/2020 | Staker et al. |
| 10,921,317 | B2 | 2/2021 | Mallick |
| 10,948,488 | B2 | 3/2021 | Mallick |
| 2003/0054408 | A1 | 3/2003 | Ravi et al. |
| 2004/0023413 | A1 | 2/2004 | Opalsky |
| 2004/0091931 | A1 | 5/2004 | Gold |
| 2006/0160234 | A1 | 7/2006 | Lopez-Avila et al. |
| 2006/0263769 | A1 | 11/2006 | Luo et al. |
| 2007/0188750 | A1 | 8/2007 | Lundquist et al. |
| 2007/0218503 | A1 | 9/2007 | Mitra |
| 2009/0214591 | A1 | 8/2009 | Manucharyan et al. |
| 2011/0065807 | A1 | 3/2011 | Radovic-Moreno et al. |
| 2011/0263688 | A1 | 10/2011 | Barany et al. |
| 2012/0077688 | A1 | 3/2012 | Bergo et al. |
| 2015/0160204 | A1 | 6/2015 | Mitra |
| 2015/0185199 | A1 | 7/2015 | Joo et al. |
| 2015/0330974 | A1 | 11/2015 | Staker et al. |
| 2016/0102344 | A1 | 4/2016 | Niemeyer et al. |
| 2016/0310926 | A1 | 10/2016 | Sun et al. |
| 2017/0044245 | A1 | 2/2017 | Meng et al. |
| 2017/0191051 | A1 | 7/2017 | Nikiforov |
| 2017/0283868 | A1 | 10/2017 | Beechem et al. |
| 2020/0025752 | A1 | 1/2020 | Gopinath et al. |
| 2020/0025757 | A1 | 1/2020 | Gopinath et al. |
| 2020/0232994 | A1 | 7/2020 | Mitra |
| 2020/0318101 | A1 | 10/2020 | Mallick et al. |
| 2021/0278400 | A1 | 1/2021 | Mallick |
| 2021/0101930 | A1 | 4/2021 | Gremyachinskiy et al. |
| 2021/0223238 | A1 | 7/2021 | Mallick |
| 2021/0239705 | A1 | 8/2021 | Mallick |
| 2021/0355483 | A1 | 11/2021 | Chee et al. |
| 2021/0373005 | A1 | 12/2021 | Mallick |

FOREIGN PATENT DOCUMENTS

| | | | | |
|---|---|---|---|---|
| WO | WO0146675 | A2 | 6/2001 | |
| WO | WO-02086081 | A2 | 10/2002 | |
| WO | WO-2006135527 | A2 | 12/2006 | |
| WO | WO-2007117444 | A2 | 10/2007 | |
| WO | WO-2010065531 | A * | 6/2010 | ........... G01N 33/543 |
| WO | WO-2010065531 | A1 | 6/2010 | |
| WO | WO-2014078855 | A1 | 5/2014 | |
| WO | WO-2015097077 | A2 | 7/2015 | |
| WO | WO-2016174525 | A1 | 11/2016 | |
| WO | WO-2017127762 | A1 | 7/2017 | |
| WO | WO-2018102759 | A1 | 6/2018 | |
| WO | WO-2019036055 | A2 | 2/2019 | |
| WO | WO-2019195633 | | 10/2019 | |
| WO | WO-2019236749 | A2 | 12/2019 | |
| WO | WO-2020106889 | A1 | 5/2020 | |
| WO | WO-2020223368 | A1 | 11/2020 | |

OTHER PUBLICATIONS

Arnold et al. "The majority of immunogenic epitopes generate CD44-T cells that are dependent on MHC class II-bound peptide-flanking residues," J Immunol, Jul. 15, 2002 (Jul. 15, 2002), vol. 169, No. 2, pp. 739-749.

Ayoglu, et al., Autoantibody Profiling in Multiple Sclerosis Using Arrays of Human Protein Fragments, Molecular & Cellular Proteomics, (12)9 Sep. 1, 2013 (Sep. 1, 2013), pp. 2657-2672, XP055294116, US, ISSN: 1535-9476, DOI: 10.1074/mcp.M112.026757.

Blatch, et al. The tetratricopeptide repeat: a structural motif mediating protein-protein interactions. Bioessays Nov. 1999;21(11):932-939.

Buenrostro, et al. Quantitative analysis of RNA-protein interactions on a massively parallel array for mapping biophysical and evolutionary landscapes. Nat Biotechnol. Jun. 2014; 32(6): 562-568.

Bunka et al. "Production and characterization of RNA aptamers specific for amyloid fibril epitopes," J Biol Chem, Sep. 18, 2007 (Sep. 18, 2007), vol. 282, No. 47, pp. 34500-34509.

Buus, et al. High-resolution mapping of linear antibody epitopes using ultrahigh-density peptide microarrays. Molecular & Cellular Proteomics 11.12 (2012): 1790-1800.

Choung, et al. Determination of B-Cell Epitopes in Patients with Celiac Disease: Peptide Microarrays. PloS one vol. 11(1) e0147777. Jan. 29, 2016, doi:10.1371/journal.pone.0147777.

Co-pending U.S. Appl. No. 17/424,435, inventors Klein; Joshua et al., filed Jul. 20, 2021.

Co-pending U.S. Appl. No. 17/496,742, inventors Gremyachinskiy; Dmitriy et al., filed Oct. 7, 2021.

Co-pending U.S. Appl. No. 17/513,877, inventors Indermuhle; Pierre et al., filed Oct. 28, 2021.

Domenyuk, et al. Plasma Exosome Profiling of Cancer Patients by a Next Generation Systems Biology Approach. Sci Rep. 2017; 7: 42741.

EP17877076.4 The Extended European Search Report dated Aug. 11, 2020.

EP18846671.8 Extended European Search Report dated Apr. 23, 2021.

Fodor, et al. Light-Directed, Spatially Addressable Parallel Chemical Synthesis. Science , vol. 251, 767-773, 1991.

Ford et al. Degenerate recognition of T cell epitopes: impact of T cell receptor reserve and stability of peptide:MHC complexes, Mol Immunol, Feb. 1, 2004 (Feb. 1, 2004), vol. 40, No. 14-15, pp. 1019-1025.

Hung, et al. Large-area spatially ordered arrays of gold nanoparticles directed by lithographically confined DNA origami. Nat Nanotechnol. Feb. 2010;5(2):121-6. doi: 10.1038/nnano.2009.450. Epub Dec. 20, 2009.

Hunniger, et al. Just in time-selection: A rapid semiautomated SELEX of DNA aptamers using magnetic separation and BEAMing. Anal Chem. Nov. 4, 2014;86(21):10940-7.

Kang, H. The prevention and handling of the missing data. Korean journal of anesthesiology vol. 64,5 (2013): 402-6. doi:10.4097/kjae.2013.64.5.402.

Laurenson, et al. Development of peptide aptamer microarrays for detection of HPV16oncoproteins in cell extracts, Analytical Biochemistry, Academic Press, Amsterdam,NL, vol. 410, No. 2, Oct. 30, 2010 (Oct. 30, 2010), pp. 161-170, XP028146256,ISSN: 0003-2697,DOI: 10.1016/J.AB.2010.10.038.

Lin et al. Development of a novel peptide microarray for large-scale epitope mapping of food allergens, Journal of Allergy and Clinical Immunology, Elsevier, Amsterdam, NL,vol. 124, No. 2, Aug. 1, 2009 (Aug. 1, 2009), pp. 315-322.e3, XP026390934, ISSN: 0091-6749,DOI: 10.1016/J.JACI.2009.05.024.

Lutz, et al. Efficient construction of therapeutics, bioconjugates, biomaterials and bioactive surfaces using azide-alkyne "click" chemistry. Adv Drug Deliv Rev. Jun. 10, 2008;60(9):958-70. doi: 10.1016/j.addr.2008.02.004. Epub Mar. 4, 2008.

Mckay, et al. Click Chemistry in Complex Mixtures: Bioorthogonal Bioconjugation. Chem Biol. Sep. 18, 2014; 21(9): 1075-1101.

Meldal, et al. Cu-catalyzed azide-alkyne cycloaddition. Chem Rev. Aug. 2008;108(8):2952-3015. doi: 10.1021/cr0783479.

(56) References Cited

OTHER PUBLICATIONS

Nonobe et al. A tabu search approach to the constraint satisfaction problem as a general problem solver. Eur. J. Oper. Res. 106 (1998): 599-623.
Patronov et al. "Peptide binding prediction for the human class II MHC allele HLA-DP2: a molecular docking approach," BMC Struct Biol, Jul. 14, 2011 (Jul. 14, 2011), vol. 11, No. 32, pp. 1-10.
PCT/US17/64322 International Search Report and Written Opinion dated Apr. 25, 2018.
PCT/US18/00364 International Search Report and Written Opinion dated Mar. 22, 2019.
PCT/US2019/025909 International Search Report and Written Opinion dated Jun. 14, 2019.
PCT/US2019/035654 International Search Report and Written Opinion dated Nov. 25, 2019.
PCT/US2019/062482 International Search Report and Written Opinion dated Mar. 3, 2020.
PCT/US2020/030501 International Search Report and Written Opinion dated Aug. 11, 2020.
Price, et al., On silica peptide microarrays for high-resolution mapping of antibody epitopes and diverse protein-protein interactions, Nature Medicine, vol. 18, No. 9, Aug. 19, 2012, pp. 1434-1440, XP055793803, New York ISSN: 1078-8956, DOI: 10.1038/nm.2913 Retrieved from the Internet:URL:http://www.nature.com/articles/nm.2913.
Reineke, et al. Epitope mapping protocols. Preface. Methods in molecular biology (Clifton, N.J.) vol. 524 (2009): v-vi.
Reyes et al. "Critical role of HLA-DR11 binding peptides' peripheral flanking residues in fully-protective malaria vaccine development," Biochem Biophys Res Commun, May 23, 2017 (May 23, 2017), vol. 489, No. 3, pp. 339-345.
Riccelli, et al. Hybridization of single-stranded DNA targets to immobilized complementary DNA probes: comparison of hairpin versus linear capture probes. Nucleic acids research vol. 29,4 (2001): 996-1004. doi:10.1093/nar/29.4.996.
Richer, et al., Epitope identification from fixed-complexity random-sequence peptide microarrays, Molecular & cellular proteomics, vol. 14, No. 1, Nov. 3, 2014, pp. 136-147.
Rothemund, et al. Folding DNA to create nanoscale shapes and patterns. Nature. Mar. 16, 2006;440(7082):297-302.
Sant'Angelo et al. "Recognition of core and flanking amino acids of MHC class II-bound peptides by the T cell receptor," Eur J Immunol, Sep. 1, 2002 (Sep. 1, 2002), vol. 32, No. 9, pp. 2510-2520.
She, et al. Comprehensive and quantitative mapping of RNA-protein interactions across a transcribed eukaryotic genome. Proc Natl Acad Sci USA. Apr. 4, 2017; 114(14): 3619-3624.
Sjoberg et al. Validation of affinity reagents using antigen microarrays, NEWBIOTECHNOLOGY, vol. 29, No. 5, Jun. 1, 2012 pp. 555-563, XP055793929, NLISSN: 1871-6784.
Speltz, et al. Design of Protein-Peptide Interaction Modules for Assembling Supramolecular Structures in Vivo and in Vitro. ACS Chem Biol. Sep. 18, 2015;10(9):2108-15. doi: 10.1021/acschembio.5b00415. Epub Jul. 17, 2015.
Stöhr, et al. A 31-residue peptide induces aggregation of tau's microtubule-binding region in cells. Nat Chem. Sep. 2017; 9(9): 874-881. Published online Apr. 3, 2017.doi: 10.1038/nchem.2754.
Tessler, L. Digital Protein Analysis: Technologies for Protein Diagnostics and Proteomics through Single-Molecule Detection (2011). All Theses and Dissertations (ETDs). 346 https://openscholarship.wustl.edu/etd/346.
U.S. Appl. No. 16/659,132 Notice of Allowance dated Jan. 14, 2021.
U.S. Appl. No. 16/659,132 Office Action dated Oct. 8, 2020.
U.S. Appl. No. 16/788,536 Notice of Allowance dated Dec. 9, 2020.
U.S. Appl. No. 16/788,536 Office Action dated Mar. 10, 2020.
U.S. Appl. No. 16/788,536 Office Action dated Sep. 24, 2020.
U.S. Appl. No. 16/791,456 Office Action dated Jul. 6, 2021.
U.S. Appl. No. 17/062,405 Final Office Action dated Aug. 24, 2021.
U.S. Appl. No. 17/062,405 Notice of Allowance dated Sep. 30, 2021.
U.S. Appl. No. 17/062,405 Office Action dated Apr. 14, 2021.
U.S. Appl. No. 17/191,632 Examiner's Interview Summary dated Nov. 9, 2021.
U.S. Appl. No. 17/191,632 Final Office Action dated Sep. 17, 2021.
U.S. Appl. No. 17/191,632 Office Action dated May 12, 2021.
U.S. Appl. No. 16/426,917 Notice of Allowance dated Oct. 1, 2019.
Wilson, et al. Single-Step Selection of Bivalent Aptamers Validated by Comparison with SELEX Using High-Throughput Sequencing. PLoS One. 2014; 9(6): e100572.
Zandian, Arash et al. Whole-Proteome Peptide Microarrays for Profiling Autoantibody Repertoires within Multiple Sclerosis and Narcolepsy. Journal of proteome research 16(3) 2017: 1300-1314.
R&D Systems (product manual from 2015) (Year: 2015).
Huang et al. (Briefings in Bioinformatics, 2012, 13(5): 586-614) (Year: 2012).
Rusmini et al. (Biomacromolecules, 2007, 8:1775-1789) (Year: 2007).
Zhao et al. (Computational Biology and Chemistry, 2015, 57:12-20) (Year: 2015).

* cited by examiner

| Whole proteome quantification: counts for all proteins ||||
|---|---|---|
| Protein | #Mol | #d-code_hits |
| Protein 1 | 106 | 10 |
| Protein 2 | 832 | 6 |
| Protein 3 | $1.6 \times 10^6$ | 30 |
| ... | | |
| Protein 25K | 1 | 22 |

FIG. 11

| anomaly list: likely mutant and modified proteins | | |
|---|---|---|
| Location | LikelyProtein | extra-code_hits |
| Spot 1,2 | Protein1 | TRT, Y', ... |
| Spot 12,36 | Protein2 | RBM, ... |
| ... | | |

FIG. 12

Identifying A Protein

>sp|P42212|GFP_AEQVI Green fluorescent protein OS=Aequorea victoria GN=GFP PE=1 SV=1  6-HIS
MSKGEELFTGVVP-IVELDGDVNGHKFSVSGEGEGDATYGK_TLKFICTTGKLPVPW>TLVTTFSYGVQCFSRYPDHMKQHDFFKSAM>EGYVQERTIFFKDGNYKTRAEVKFEG
DT_VNRIELKGIDFKEDGNIIGHKLEYNYNSHNVYIMADKQKNGIKVNFKIRHNIEDGSVQLADHYQQNTPIGDGPVLLPDNHY_STQSALSKDPNEKRDHMVLLEFVTAAGITHG
MDELYKHHHHHH >sp|P61823|RNAS1_BOVIN Ribonuclease pancreatic OS=Bos taurus GN=RNASE1 PE=1 SV=1
MA_KSIVLLSLLVLVLLLVRVQPSLGKETAAAKFERQHMDSSTSAASSSNYCNQMMKSRNLTKDRCKPVNTFVHESLADVQAVCSQKNVACKNGQTNCYQSYS™MSIT>CRETGSS
KYPNCAYKT"QANKHIIVACEGNPYVPVHFDASV >sp|P02788|TRFL_HUMAN Lactotransferrin GS=Homo sapiens GN=LTF PE=1 SV=6
MK_VFLVLLFLGALGICLAGRRRSVQMCAVSQPEATKCFQWQRNMRKVRGPPVSCIKRDSPIQC-QAIAENRADAVTLDGGFIYEAGLAPYK_RPVAAEVYGTERQPRTHYAVAV
VKKGGS=QLNELQGLKSCHTGLRRTAGWNVPIGTLRPFLNWTGPPEPIEAAVARFSASCV>GADKGQFPNLCRLCAGTGENKCAFSSQEPYFSYSGAFKCLRDGAGDVAFIREST
VFEDLSDEAERE>EYELLCPDNTRKPVDKFKDCHLARVPSHAVVARSVNGKEDAIWNLLRQAQEKFGKDKSPKFQLFGSPSGQKD_LFKDSAIGFSRVPPRIDSGLYLGSGYFTAIQ
NLRKSEEEVAARRARVVWCAVGEQELRKCNQWSGLSEGSVTCSSASTTEDCIALVLKGEADAMSLDGGYVYTAGKCGLVPVLAENYKSQQSSDPDPNCVDRPVEGYLAVAVVRRSD
TS_TWNSVKGKKSCHTAV>RTAGWNIPMGLLFNQTGSCKFDEYFSQSCAPGSDPRSNLCALCIGDEQGENKCVPNSNERYYGYTGAFRCLAENAGDVAFVKDV-VLQNTDGNNNEA
WAKDLKLADFALLCLDGKRKPVTFARSCHLAMAPNHAVVSRMDKVERLKQVLLHQQAKFGRNGSDCPDKFCLFQSETKNLLFNDNTECIARLHGKTTYEKYIGPQYVAGITNLKKC
STSPLLEACEFIRK >tr|C_L9P'_|C1L9P1_SCHJA Glutathione S-transferase M1 OS=Schistosoma japonicum GN=GSTM1 PE=2 SV=1 HIS-V5-GSTM1
CAX71422 SJCD00671637
STMSP-LGYWKIKGLVQPTRLLLFYLEEKYEEHLYERDEGDKWRNKKFE_GLEFPNL>YYIDGDVKLTQSMAIIRYIADKHNMLGGCPKFRAEISMLEGAVLD-RYGVSRIAYSKD
FETLKVDFLSKLPEMIKMFEDRLICHKTYLNGDHVTHPDFMLYDALDVVLYMDPMCLDAFPKLVCFKKRIEAIPQIDKYLKSSKYIAWPLQGWQATFGGGDHPPKSDLVPRGSPLEV
LFQGPCGSYGS

FIG. 18

METHODS OF ASSAYING PROTEINS

CROSS-REFERENCE

This application is a continuation application of U.S. Non-Provisional application Ser. No. 17/191,632, filed Mar. 3, 2021, which is a continuation application of U.S. Non-Provisional application Ser. No. 17/153,877, filed Jan. 20, 2021, which is a continuation application of U.S. Non-Provisional application Ser. No. 16/659,132, filed Oct. 21, 2019, now U.S. Pat. No. 10,948,488, which is a continuation application of U.S. Non-Provisional application Ser. No. 16/426,917, filed May 30, 2019, now U.S. Pat. No. 10,473,654, which is a continuation of International Patent Application No. PCT/US2017/064322, filed on Dec. 1, 2017, which claims priority to U.S. Provisional Application No. 62/429,063, filed Dec. 1, 2016, and U.S. Provisional Application No. 62/500,455, filed May 2, 2017, each of which applications is incorporated herein by reference in its entirety.

SEQUENCE LISTING

The instant application contains a Sequence Listing which has been submitted electronically in ASCII format and is hereby incorporated by reference in its entirety. Said ASCII copy, created on Jan. 20, 2021, is named 51612-701_304_Seq_List.txt and is 15,016 bytes in size.

BACKGROUND OF THE INVENTION

Current techniques for protein identification typically rely upon either the binding and subsequent readout of highly specific and sensitive antibodies or upon peptide-read data (typically on the order of 12-30 AA long) from a mass spectrometer.

SUMMARY OF THE INVENTION

The present disclosure provides methods and systems for assaying proteins. In some embodiments, the present disclosure provides approaches in which the identities of proteins, i.e. their sequence, in a mixture are inferred from a series of measurements that may be highly incomplete and/or are not specific to a particular protein. Methods and systems described herein may also be used to characterize and/or identify biopolymers, including proteins. Additionally, methods and systems described herein may be used to identify proteins more quickly than techniques for protein identification that rely upon data from a mass spectrometer. In some examples, methods and systems described herein may be used to identify at least 400 different proteins with at least 50% accuracy at least 10% more quickly than techniques for protein identification that rely upon data from a mass spectrometer. In some examples, methods and systems described herein may be used to identify at least 1000 different proteins with at least 50% accuracy at least 10% more quickly than techniques for protein identification that rely upon data from a mass spectrometer.

An aspect of the invention provides a method of determining protein characteristics. The method comprises obtaining a substrate with portions of one or more proteins conjugated to the substrate such that each individual protein portion has a unique, resolvable, spatial address. In some cases, each individual protein portion may have a unique, optically resolvable, spatial address. The method further comprises applying a fluid containing a first through nth set of one or more affinity reagents to the substrate. In some embodiments, the affinity reagents may contain or be coupled to an identifiable tag. After each application of the first through nth set of one or more of affinity reagents to the substrate, the method comprises performing the following steps: observing the affinity reagent or identifiable tag; identifying one or more unique spatial addresses of the substrate having one or more observed signal; and determining that each portion of the one or more proteins having an identified unique spatial address contains the one or more epitopes associated with the one or more observed signals. In some instances, each of the conjugated portions of the one or more proteins is associated with an unique spatial address on the substrate. In some instances, each affinity reagent of the first through nth set of one or more affinity reagents is not specific to an individual protein or protein family. In some instances, the binding epitope of the affinity reagent is not known or specific to an individual protein or protein family.

In some cases, the methods of this disclosure may also be used with a substrate which has multiple proteins bound in a single location, wherein at least about 50%, 60%, 70%, 80%, 90%, or more than 90% of the proteins at a single location comprise a common amino acid sequence. In some cases, the methods of this disclosure may also be used with a substrate which has multiple proteins bound in a single location, wherein at least about 50%, 60%, 70%, 80%, 90%, or more than 90% of the proteins at a single location comprise at least 95% amino acid sequence identity.

In some embodiments, the one or more proteins may comprise one single protein molecule. In some embodiments, the one or more proteins may comprise bulk proteins. In some embodiments, the one or more proteins may comprise a plurality of a same protein that is conjugated at a same unique spatial address on the substrate.

In some embodiments, each affinity reagent of the first through nth set of one or more affinity reagents recognizes a family of one or more epitopes that are present in more than one proteins. In some embodiments, the method further comprises determining the identity of the portion of the one or more proteins to a threshold degree of accuracy based on the determined one or more epitopes within the portion. In some instances, the first through nth set of one or more affinity reagents comprises more than 100 affinity reagents. In some embodiments the method further comprises the use of affinity reagents which bind a single protein or single protein isoform.

In some embodiments, the method further comprises determining the identity of the portion of the one or more proteins to a threshold degree of accuracy based on the pattern of binding of the affinity reagents. In some instances the substrate is a flow cell. In some instances, the portions of one or more proteins are conjugated to the substrate using a photo-activatable linker. In some instances, the portions of one or more proteins are conjugated to the substrate using a photo-cleavable linker.

In some instances, at least a portion of the at least one set of affinity reagents is modified to be conjugated to an identifiable tag. In some instances the identifiable tag is a fluorescent tag. In some instances the identifiable tag is a magnetic tag. In some instances an identifiable tag is a nucleic acid barcode. In some instances an identifiable tag is an affinity tag (e.g. Biotin, Flag, myc). In some instances, the number of spatial addresses occupied by an identified portion of a protein is counted to quantify the level of that protein in the sample. In some instances, the identity of the portion of the one or more proteins is determined using deconvolution software. In some instances, the identity of the portion of the one or more proteins is determined by decoding combinations of epitopes associated with unique spatial addresses. In some instances, the method further comprises denaturing the one or more proteins prior to conjugating the portions of the one or more proteins to the substrate. In some instances, the portions of one or more proteins to a substrate are present in a complex mixture of multiple proteins. In some instances, the method is used to identify multiple proteins.

An additional aspect of the invention provides a method of identifying a protein comprising: acquiring a panel of affinity reagents none of which are specific for a single protein or family of proteins, determining the binding properties of the antibodies in the panel, iteratively exposing the protein to the panel of antibodies, determining a set of the antibodies which bind the protein, and using one or more deconvolution methods based on the known binding properties of the antibodies to match the set of antibodies to a sequence of a protein, thereby determining the identity of the protein. In some instances, the protein to be identified is identified within a sample containing multiple different proteins. In some instances, the method is able to simultaneously identify multiple proteins within a single sample.

Another aspect of the invention provides a method of identifying a protein. The method comprises acquiring a panel of antibodies none of which are specific for a single protein or family of proteins, determining the binding properties of the antibodies in the panel, iteratively exposing the protein to the panel of antibodies, determining a set of the antibodies which do not bind the protein, and using one or more deconvolution methods based on the known binding properties of the antibodies to match the set of antibodies to a sequence of a protein, thereby determining the identity of the protein.

Another aspect of the invention provides a method of uniquely identifying and quantifying n proteins in a mixture of proteins using m affinity reagents, wherein n is larger than m, and n and m are positive integers greater than 1, and wherein the proteins have not been separated by an intrinsic property. In some instances, n is approximately 5, 10, 20, 50, 100, 500, 1,000, 5,000, or 10,000 times larger than m.

Another aspect of the invention provides a method of uniquely identifying and quantifying n proteins in a mixture of proteins using m binding reagents, wherein n is larger than m, and wherein the proteins are randomly arranged. In some instances, the proteins have not been separated by a size based, or charge based, separation method.

Another aspect of the invention provides a method of uniquely identifying and quantifying n single protein molecules in a mixture of protein molecules using m affinity reagents. The method further comprises that n is larger than m, and that the single protein molecules are conjugated to a substrate and spatially separated such that each individual protein molecule has a unique, optically resolvable, spatial address.

Another aspect of the invention provides a method to identify, with certainty above a threshold amount, an unknown single protein molecule from a pool of n possible proteins. The method comprises using a panel of affinity reagents, wherein the number of affinity reagents in the panel is m, and wherein m is less than one tenth of n.

Another aspect of the invention provides a method to select a panel of m affinity reagents capable of identifying an unknown protein selected from a pool of n possible proteins, wherein m is less than n−1.

Another aspect of the invention provides a method to select a panel of m affinity reagents capable of identifying an unknown protein selected from a pool of n possible proteins, wherein m is less than one tenth of n.

Another aspect of the invention provides a method to select a panel of less than 4000 affinity reagents, such that the panel of less than 4000 affinity reagents is capable of uniquely identifying each of 20,000 different proteins.

Another aspect of the invention provides a method of uniquely identifying and quantifying n proteins in a mixture of proteins using m binding reagents, wherein m is less than n−1, and wherein each protein is identified via a unique profile of binding by a subset of the m the binding reagents.

In some instances, the method is capable of identifying more than 20% of proteins in the human proteome from a human protein sample, wherein the proteins are not substantially destroyed in the process. In some instances, the method is capable of identifying more than 20% of proteins in the proteome for any organism with an available protein sequence database (e.g. yeast, E. coli, C. elegans). In some instances, a protein sequence database may be generated by genome, exome, and/or transcriptome sequencing. In some instances, the method does not require more than 4000 affinity reagents. In some instances, the method does not require more than 100 mg of the protein sample.

Another aspect of the invention provides a method of uniquely identifying a single protein molecule. The method comprises obtaining a panel of affinity reagents, exposing the single protein molecule to each of the affinity reagents in the panel, determining whether each affinity reagent binds or does not bind the single protein molecule, and using the collected binding data to determine the identity of the single protein molecule. Additionally, in some embodiments, the identity of the single protein molecule cannot be determined by the binding data of any individual affinity reagent in the panel of affinity reagents. In some instances, affinity reagents with overlapping binding characteristics may be used to enrich affinity for any particular target.

Another aspect of the invention provides a method of determining protein characteristics. The method comprises conjugating portions of one or more proteins to a substrate, wherein each of the conjugated portions of the one or more proteins is associated with an unique spatial address on the substrate. In some examples, a unique spatial address may be a spatial address that is associated with a particular portion of a protein. The method also comprises applying a first through nth set of one or more affinity reagents to the substrate, wherein each affinity reagent of the first through nth set of one or more affinity reagents recognizes an epitope that is between one and ten residues in length, and wherein each affinity reagent of the first through nth set of one or more of affinity reagents is linked to an identifiable tag. Additionally, the method comprises that after each application of the first through nth set of one or more of affinity reagents to the substrate, the following steps are performed: observing the identifiable tag; identifying one or more unique spatial addresses of the substrate having one or more observed signal; and determining that each portion of the one or more proteins having an identified unique spatial address contains the one or more epitopes associated with the one or more observed signals.

Another aspect of the invention provides a method of determining protein characteristics. The method comprises conjugating portions of one or more proteins to a substrate, wherein each of the conjugated portions of the one or more proteins is associated with an unique spatial address on the substrate. The method also comprises applying a first through nth set of one or more affinity reagents to the substrate, wherein each affinity reagent of the first through nth set of one or more affinity reagents recognizes a family of one or more epitopes that are present in one or more proteins, and wherein each affinity reagent of the first through nth set of one or more of affinity reagents is linked to an identifiable tag. Further, the method comprises that after each application of the first through nth set of one or more affinity reagents to the substrate, the following steps are performed: observing the identifiable tag; identifying one or more unique spatial addresses of the substrate having an observed signal; and determining that each portion of the one or more proteins having an identified unique spatial address contains the epitope.

A further aspect of the invention provides a method of identifying a protein, the method comprising: acquiring a panel of affinity reagents of a known degree of nonspecificity, determining the binding properties of the affinity reagents in the panel, iteratively exposing the protein to the panel of affinity reagents, determining a set of the affinity reagents which bind the protein, and using one or more deconvolution methods based on the known binding properties of the affinity reagents to match the set of affinity reagents to a sequence of a protein, thereby determining the identity of the protein.

Additionally, another aspect of the invention provides a method of identifying a protein, the method comprising acquiring a panel of affinity reagents of a known degree of nonspecificity, determining the binding properties of the affinity reagents in the panel, iteratively exposing the protein to the panel of affinity reagents, determining a set of the affinity reagents which do not bind the protein, and using one or more deconvolution methods based on the known binding properties of the affinity reagents to match the set of affinity reagents to a sequence of a protein, thereby determining the identity of the protein.

In a further aspect, provided herein is a composition of a protein assay array, the composition comprising a substrate having a plurality of n protein molecules from a biological sample conjugated to the substrate such that each individual protein of the plurality of n protein molecules is spatially separated from each other protein of the plurality of n protein molecules, and wherein each protein of the plurality of n protein molecules is individually optically resolvable, in a first configuration, a first plurality of affinity reagent pools within a liquid medium in communication with the substrate, wherein the liquid medium is in communication with the plurality of n protein molecules conjugated to the substrate, wherein a portion of the affinity reagents within the first plurality of affinity reagent pools bound or attached to zero or more of the n protein molecules, and in a second configuration, a second plurality of affinity reagent pools within a liquid medium in communication with the substrate, wherein the liquid medium is in communication with the plurality of n protein molecules conjugated to the substrate, wherein a portion of the affinity reagents within the second plurality of affinity reagent pools are bound or attached to zero or more of the n protein molecules, wherein the binding of the affinity reagent pools to the plurality of n protein molecules is distinct between the first and second plurality of affinity reagent pools, and wherein the affinity reagent pools comprise a known degree of nonspecificity and are configured to bind to one or more epitopes of at least one protein molecule of the plurality of n protein molecules.

In some embodiments, the composition further comprises, in a third configuration, a third plurality of affinity reagent pools within a liquid medium in communication with the substrate, wherein the liquid medium is in communication with the plurality of n protein molecules conjugated to the substrate, wherein a portion of the affinity reagents within the third plurality of affinity reagent pools are bound or attached to at least a portion of the plurality of n protein molecules, wherein the binding of the affinity reagent pools to the plurality of n protein molecules is distinct between the first, second, and third plurality of affinity reagent pools. In some embodiments, the composition further comprises, in a fourth configuration, a fourth plurality of affinity reagent pools within a liquid medium in communication with the substrate, wherein the liquid medium is in communication with the plurality of n protein molecules conjugated to the substrate, wherein a portion of the affinity reagents within the fourth plurality of affinity reagent pools are bound or attached to at least a portion of the plurality of n protein molecules, wherein the binding of the affinity reagent pools to the plurality of n protein molecules is distinct between the first, second, third, and fourth plurality of affinity reagent pools. In some embodiments, the composition further comprises, in a fifth configuration, a fifth plurality of affinity reagent pools within a liquid medium in communication with the substrate, wherein the liquid medium is in communication with the plurality of n protein molecules conjugated to the substrate, wherein a portion of the affinity reagents within the fifth plurality of affinity reagent pools are bound or attached to at least a portion of the plurality of n protein molecules, wherein the binding of the affinity reagent pools to the plurality of n protein molecules is distinct between the first, second, third, fourth, and fifth plurality of affinity reagent pools.

In some embodiments, the first and second plurality of affinity reagent pools comprises one affinity reagent pool. In some embodiments, the composition further comprises first and second plurality of affinity reagent pools comprises two or more affinity reagent pools.

In some embodiments, each affinity reagent comprises an identifiable tag. In some embodiments, the identifiable tag is selected from the group consisting of a fluorescent tag, a magnetic tab, a bioluminescent protein tag, a nucleic acid tag, and a nanoparticle. In some embodiments, the identifiable tag is a nucleic acid barcode.

In some embodiments, each individual protein of the plurality of n protein molecules is conjugated to the substrate at a unique spatial address. In some embodiments, the binding of the affinity reagent pools to the plurality of n protein molecules is determined by an observation of an identifiable tag at each unique spatial address.

In some embodiments, the observation of an identifiable tag comprises an observation of a signal from the identifiable tag. In some embodiments, the observation of the signal from the identifiable tag comprises a detection of the signal from the identifiable tag. In some embodiments, the observation of the signal from the identifiable tag comprises no detection of the signal from the identifiable tag. In some embodiments, the signal comprises a fluorescence signal or a bioluminescence signal.

In some embodiments, the known degree of binding nonspecificity is a high binding specificity. In some embodiments, each affinity reagent pool recognizes a single epitope. In some embodiments, the known degree of binding nonspecificity is a low binding specificity. In some embodiments, the each affinity reagent pool recognizes two or more epitopes. In some embodiments, the different epitopes comprise different three amino acid sequences. In some embodiments, each affinity reagent pool recognizes a family of epitopes.

In some embodiments, each individual protein of the plurality of n protein molecules is conjugated to the substrate by a chemical linker. In some embodiments, the chemical linker comprises a nucleic acid. In some embodiments, the nucleic acid comprises a nucleic acid nanoball. In some embodiments, the nucleic acid is attached to the substrate by adsorption or conjugation. In some embodiments, the chemical linker comprises a photoactivatable crosslinker.

In some embodiments, the composition further comprises, in a third configuration, a liquid medium comprising a wash buffer in communication with the substrate, wherein a portion of the affinity reagents from the first and second affinity reagent pools are not bound or not attached to the n protein molecules. In some embodiments, the wash buffer removes affinity reagents bound or attached by non specific binding. In some embodiments, the wash buffer removes affinity reagents from the first or second configuration that are bound or attached to the plurality of n protein molecules.

In some embodiments, the substrate comprises an ordered array of functional groups configured to chemically attach the plurality of n protein molecules to the substrate

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 11 illustrates proteome quantification in accordance with some embodiments;

FIG. 12 illustrates an example of an anomaly list, in accordance with some embodiments;

FIG. 18 illustrates a schematic for identification of a protein, in accordance with embodiments herein. FIG. 18 discloses SEQ ID NOS 12-15, respectively, in order of appearance.

DETAILED DESCRIPTION OF THE INVENTION

Figure 1:
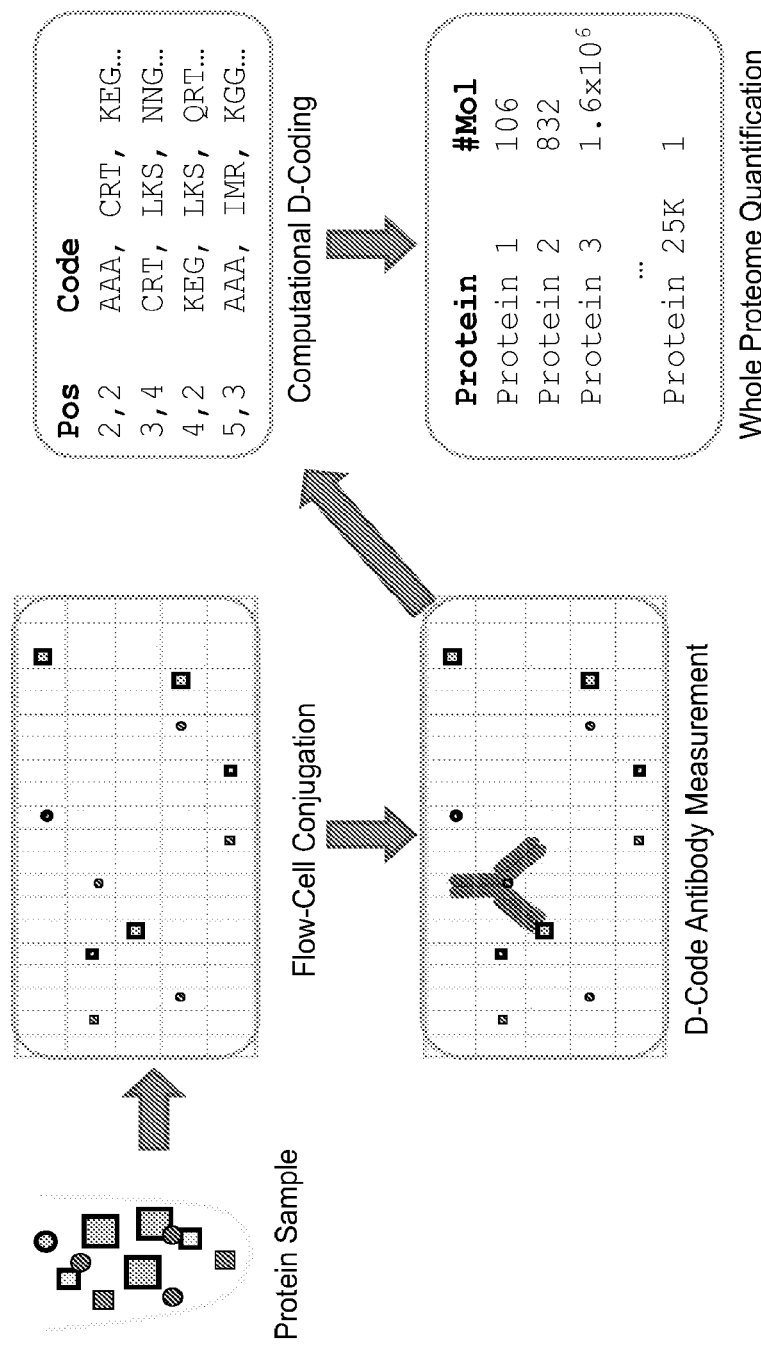
FIG. 1 illustrates a first schematic of protein quantification by anti-peptide antibody decoding, in accordance with some embodiments.
Figure 2:
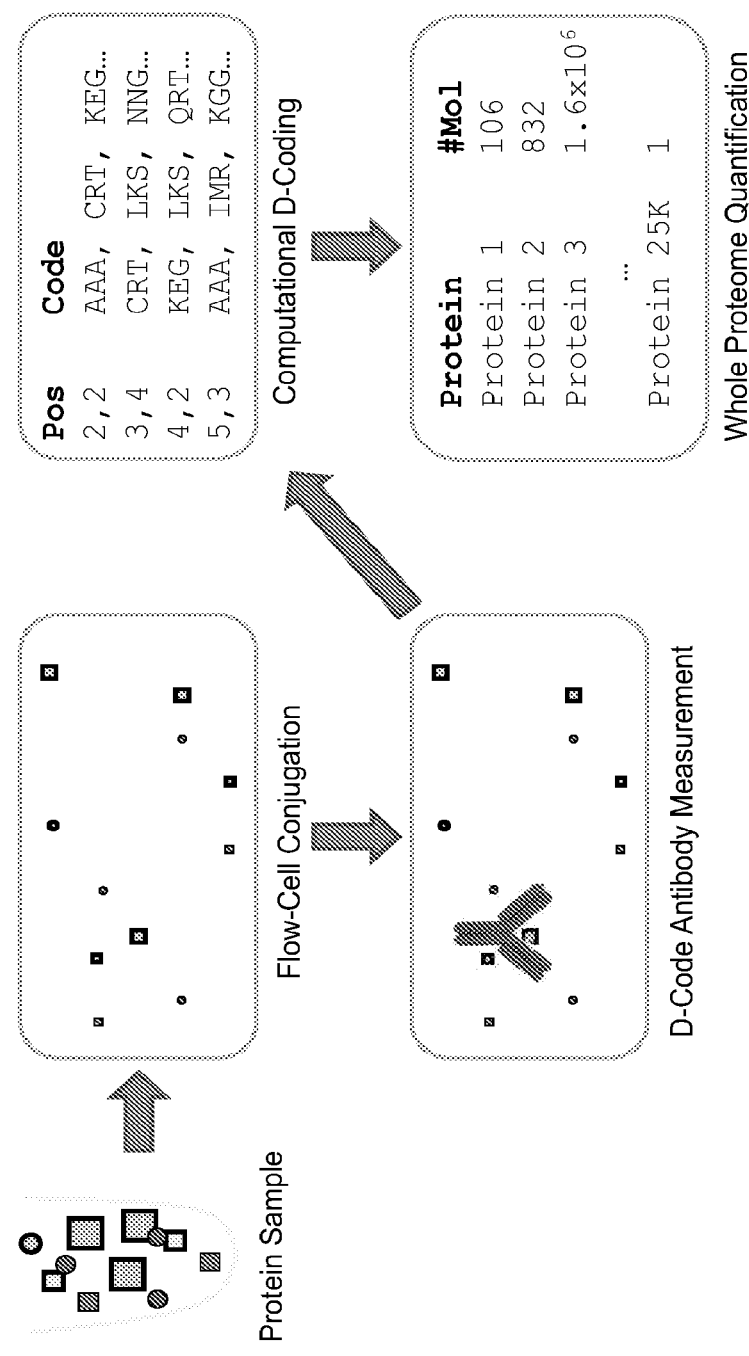
FIG. 2 illustrates a second schematic of protein quantification by anti-peptide antibody decoding, in accordance with some embodiments.
Figure 3:
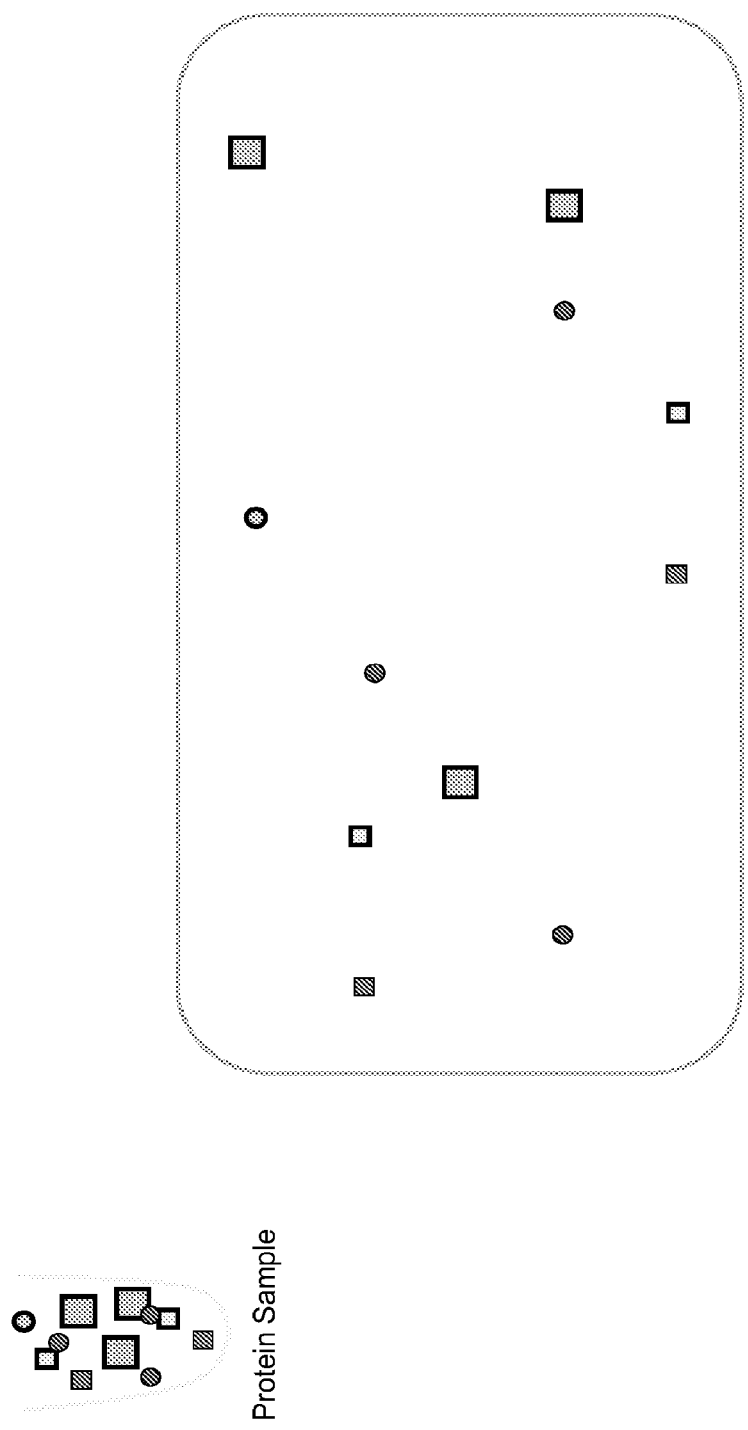
FIG. 3 illustrates flow cell conjugation, in accordance with some embodiments.
Figure 4:
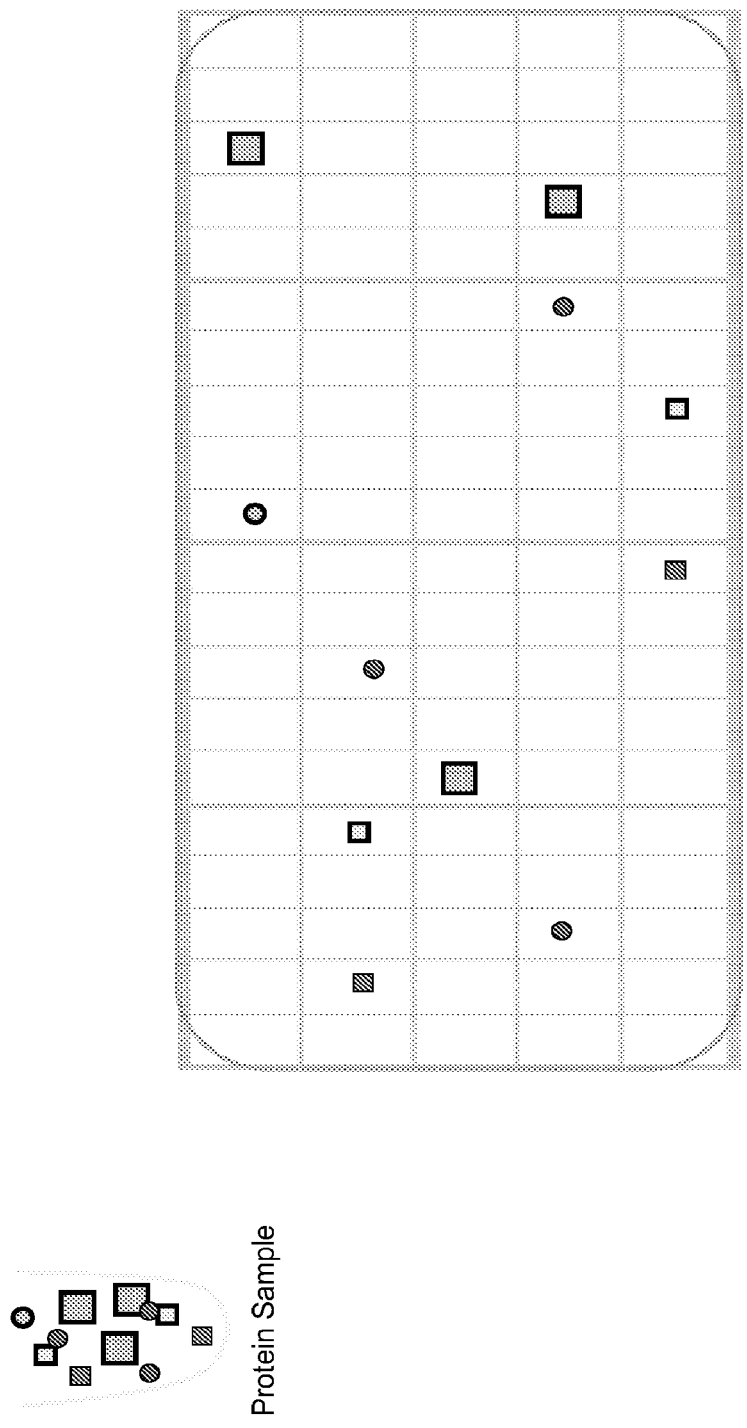
FIG. 4 illustrates a grid of unique spatial addresses on a flow cell, in accordance with some embodiments.
Figure 5:
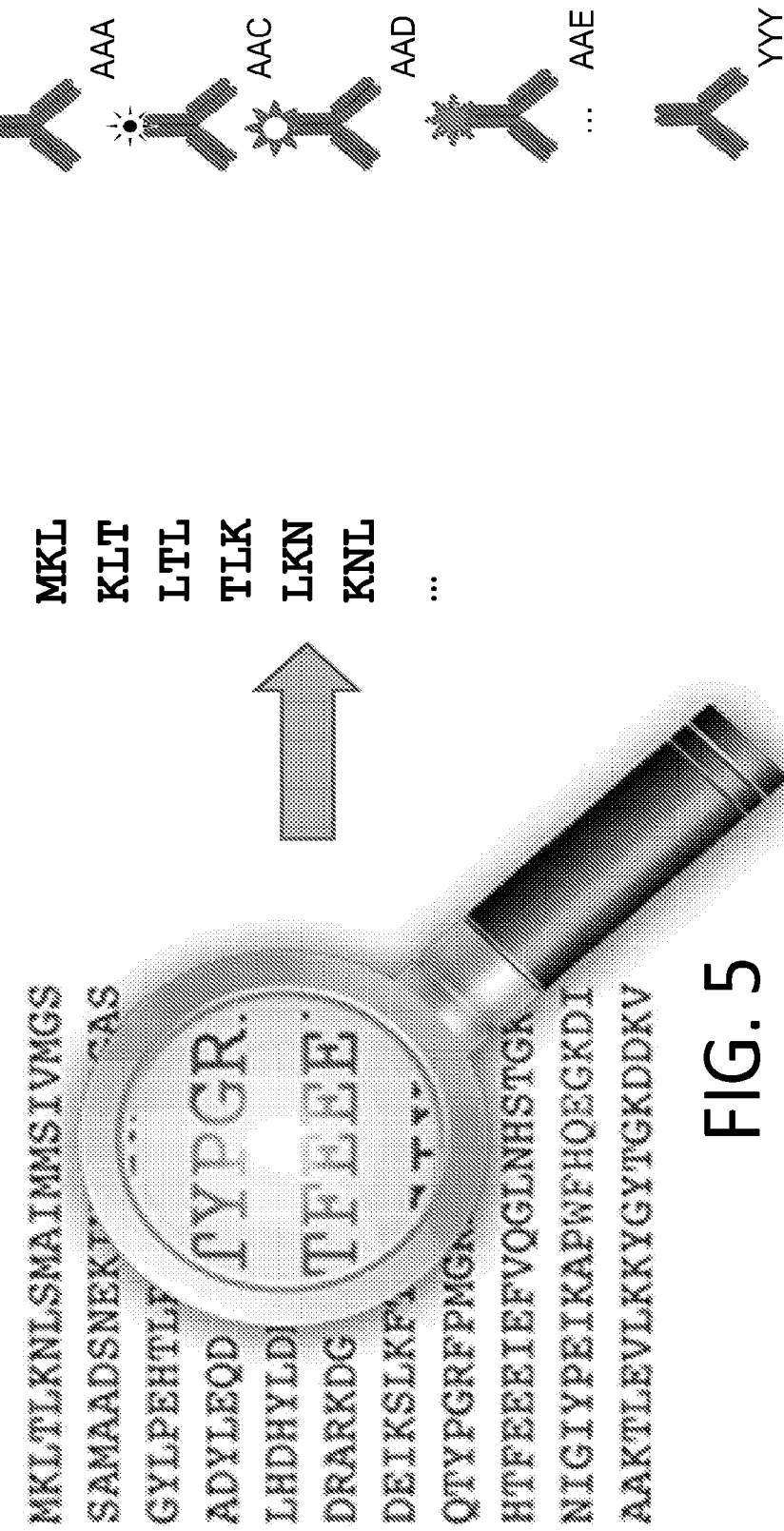
FIG. 5 illustrates de-constructing a protein (SEQ ID NOS 1-11, respectively, in order of appearance) as sets of peptides that can be matched with d-code antibodies, in accordance with some embodiments.
Figure 6:
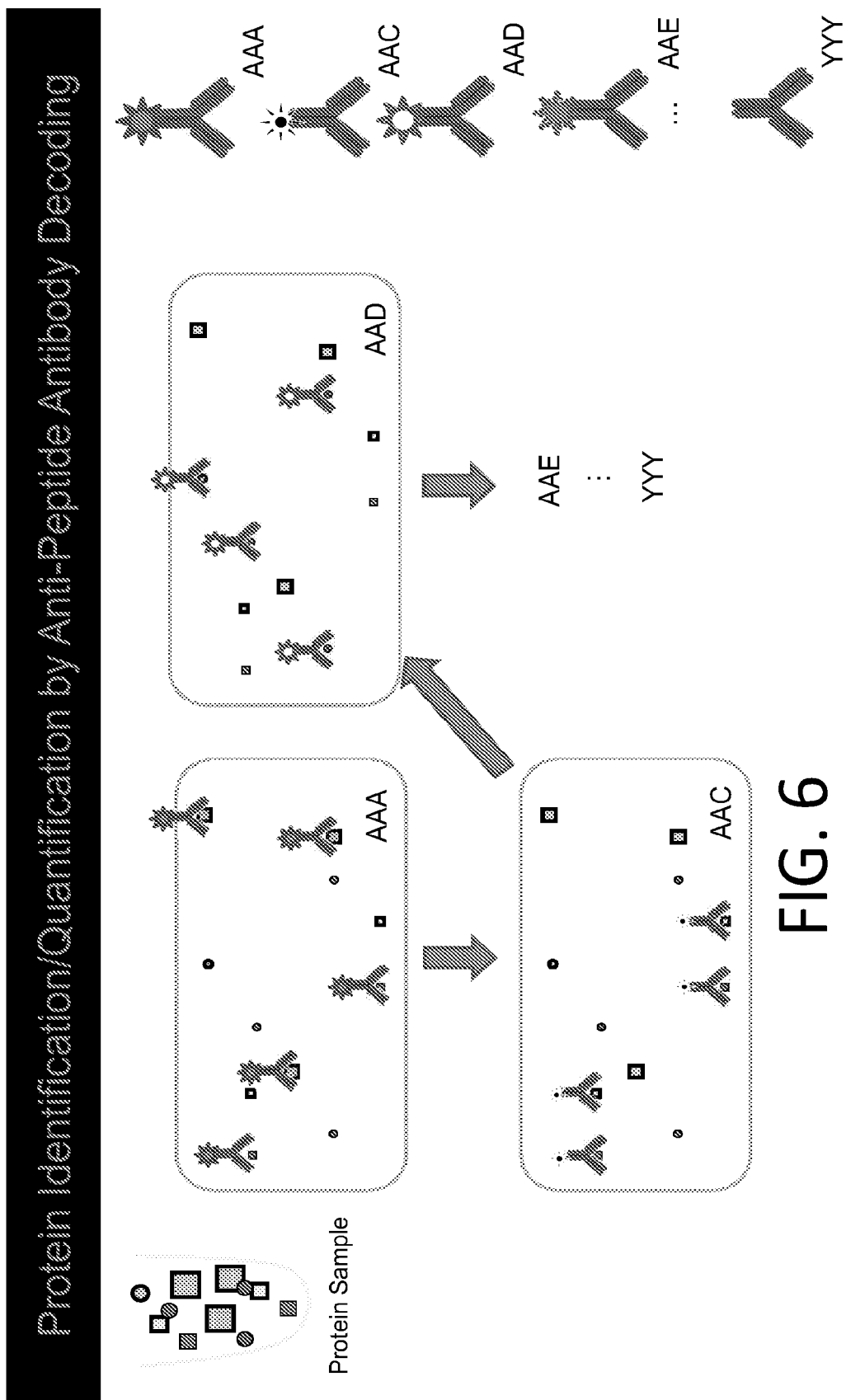
FIG. 6 illustrates a schematic of protein identification/quantification by anti-peptide antibody decoding, in accordance with some embodiments.
Figure 7:
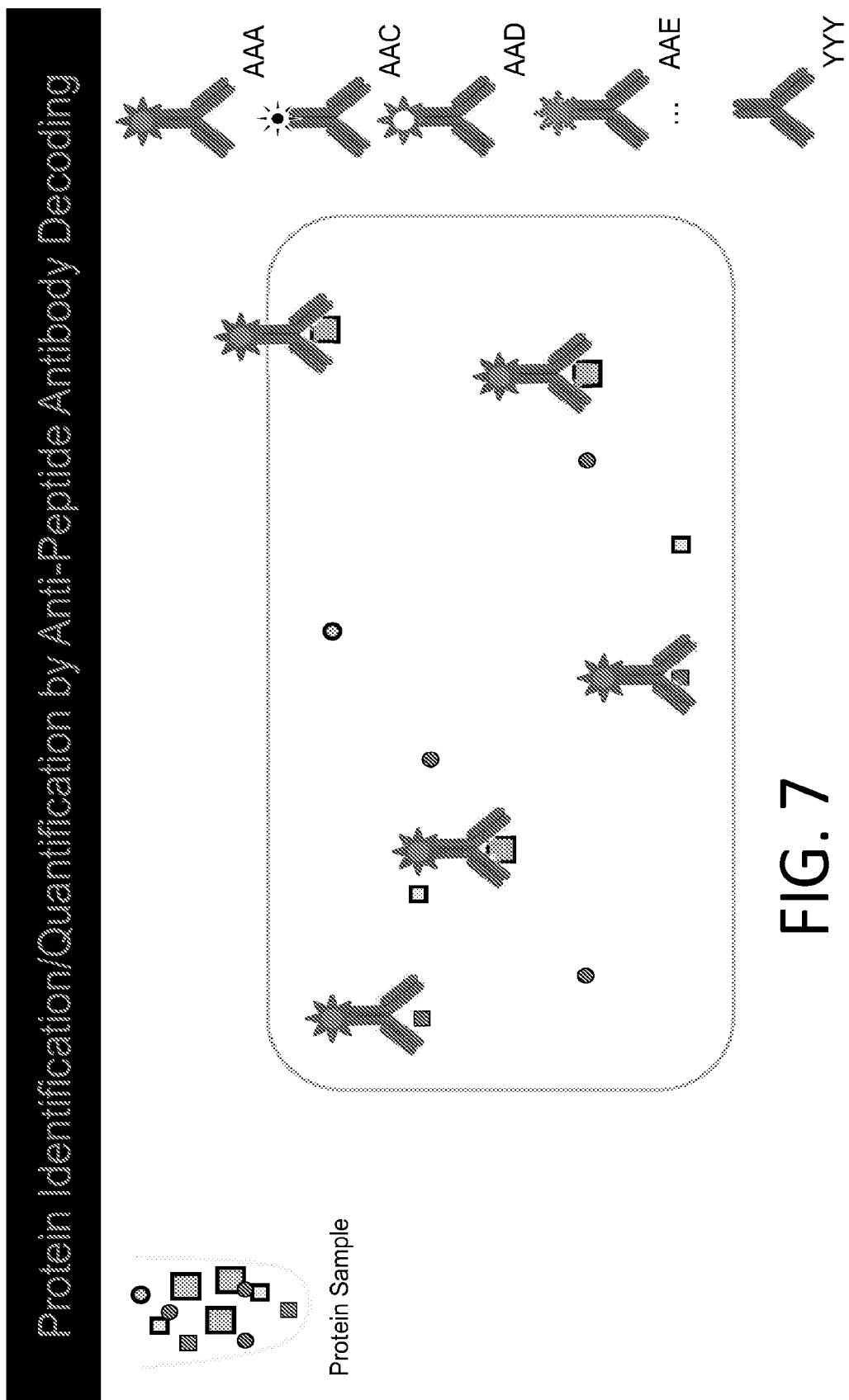
FIG. 7 illustrates observation of a first set of anti-peptide antibodies, in accordance with some embodiments.
Figure 8:
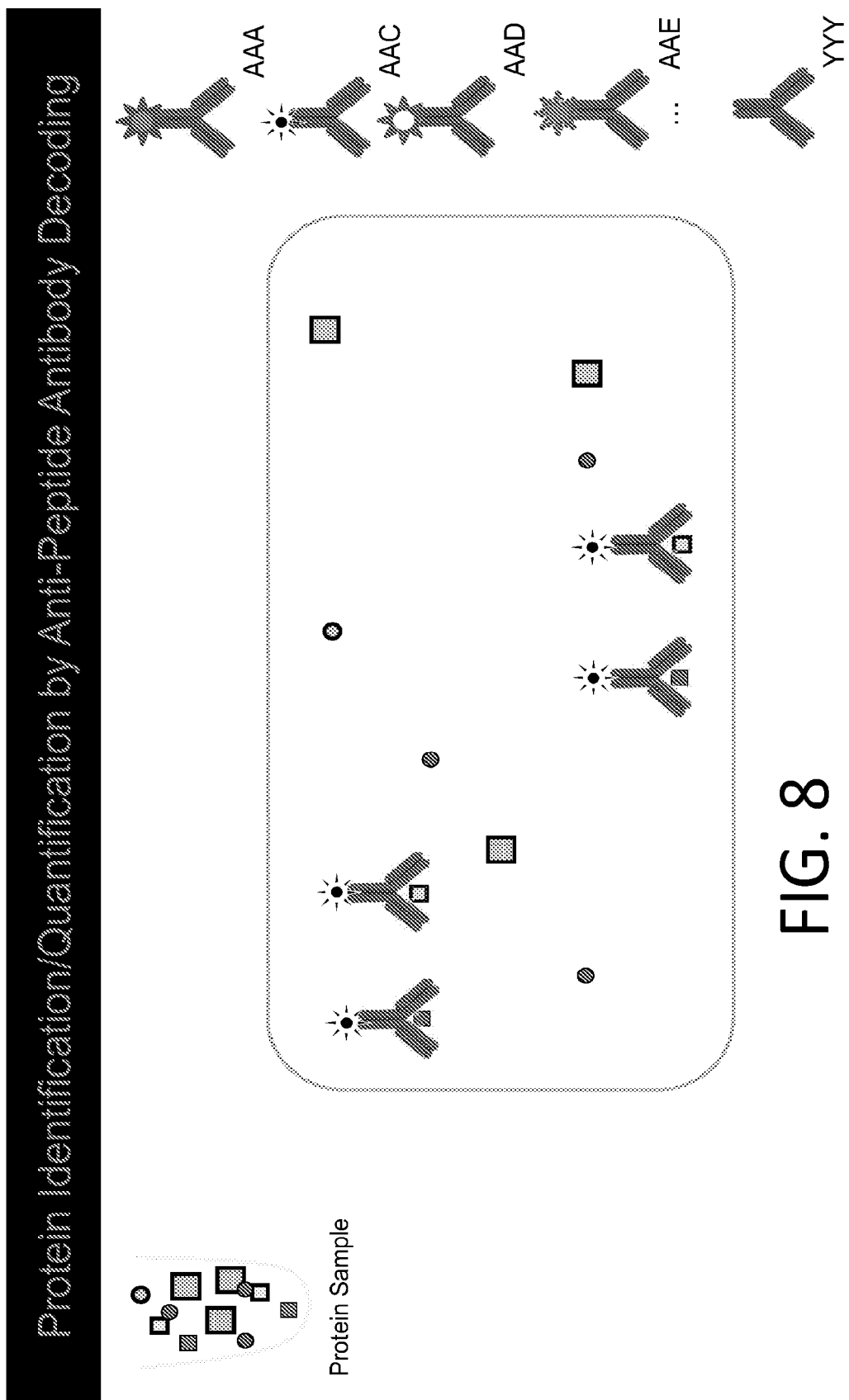
FIG. 8 illustrates observation of a second set of anti-peptide antibodies, in accordance with some embodiments.
Figure 9:
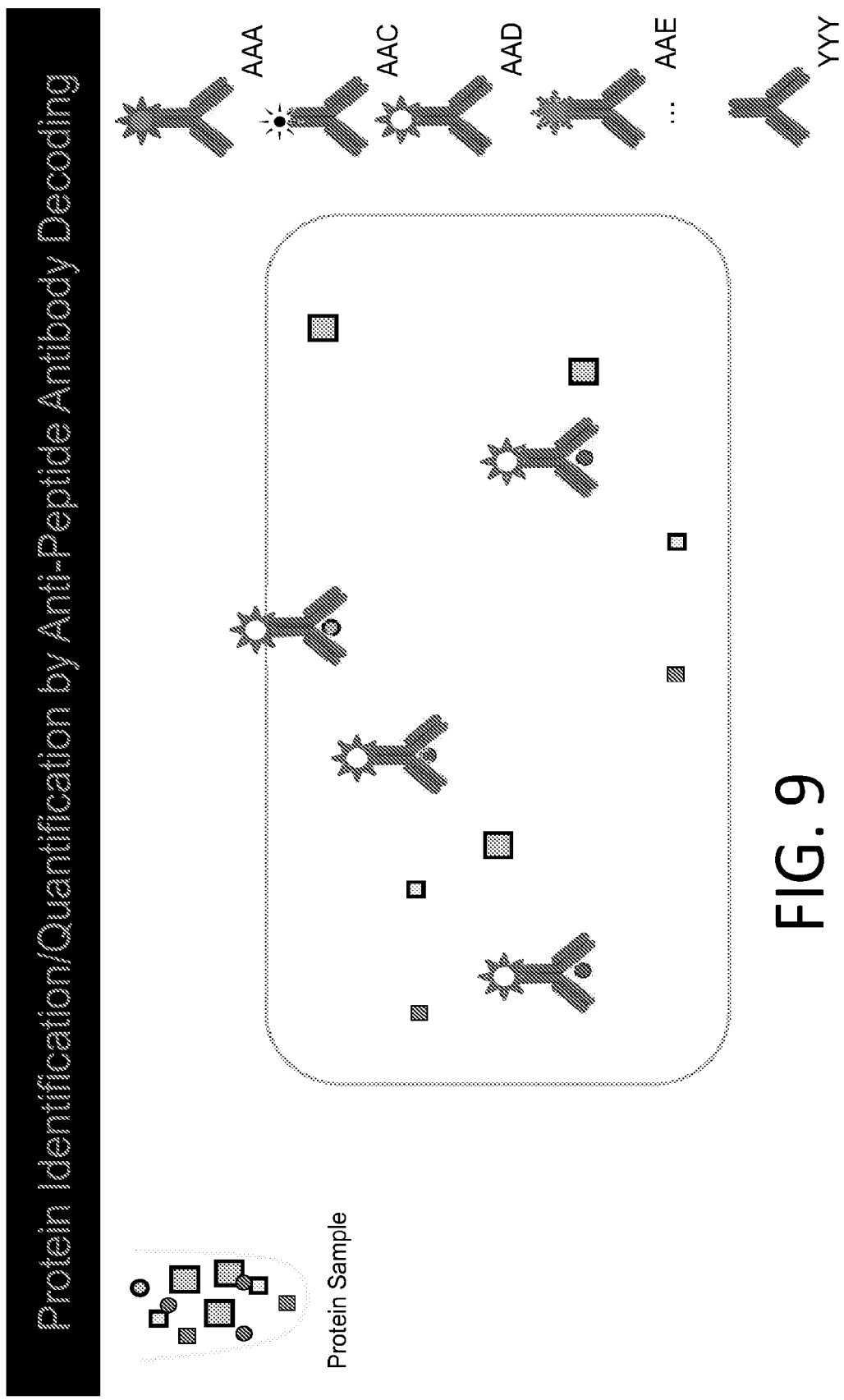
FIG. 9 illustrates observation of a third set of anti-peptide antibodies, in accordance with some embodiments.

In some examples, the approach can comprise three aspects: 1) an addressable substrate in which proteins and/or protein fragments can be conjugated; 2) a set of affinity reagents, e.g. where each affinity reagent can bind to a peptide with varying specificity; and 3) a software that is able to use a combination of prior knowledge about the binding characteristics of the affinity reagents, the specific pattern of binding of affinity reagents at each address in the substrate, and/or a database of the possible sequences of the proteins in the mixture (e.g. the human proteome) to infer the identity of a protein at a precise spatial address in the substrate. In some examples, the precise spatial address may be an unique spatial address.

Samples

The samples may be any biological sample containing protein. The samples may be taken from tissue or cells or from the environment of tissue or cells. In some examples, the sample could be a tissue biopsy, blood, blood plasma, extracellular fluid, cultured cells, culture media, discarded tissue, plant matter, synthetic proteins, archael, bacterial and/or viral samples, fungal tissue, archaea, or protozoans. In some examples, the protein is isolated from its primary source (cells, tissue, bodily fluids such as blood, environmental samples etc) during sample preparation. The protein may or may not be purified from its primary source. In some cases the primary source is homogenized prior to further processing. In some cases cells are lysed using a buffer such as RIPA buffer. Denaturing buffers may also be used at this stage. The sample may be filtered or centrifuged to remove lipids and particulate matter. The sample may also be purified to remove nucleic acids, or may be treated with RNases and DNases. The sample may contain intact proteins, denatured proteins, protein fragments or partially degraded proteins.

The sample may be taken from a subject with a disease or disorder. The disease or disorder may be an infectious disease, an immune disorder or disease, a cancer, a genetic disease, a degenerative disease, a lifestyle disease, an injury, a rare disease or an age related disease. The infectious disease may be caused by bacteria, viruses, fungi and/or parasites. Non-limiting examples of cancers include Bladder cancer, Lung cancer, Brain cancer, Melanoma, Breast cancer, Non-Hodgkin lymphoma, Cervical cancer, Ovarian cancer, Colorectal cancer, Pancreatic cancer, Esophageal cancer, Prostate cancer, Kidney cancer, Skin cancer, Leukemia, Thyroid cancer, Liver cancer, and Uterine cancer. Some examples of genetic diseases or disorders include, but are not limited to, cystic fibrosis, Charcot-Marie-Tooth disease, Huntington's disease, Peutz-Jeghers syndrome, Down syndrome, Rheumatoid arthritis, and Tay-Sachs disease. Non-limiting examples of lifestyle diseases include obesity, diabetes, arteriosclerosis, heart disease, stroke, hypertension, liver cirrhosis, nephritis, cancer, chronic obstructive pulmonary disease (copd), hearing problems, and chronic backache. Some examples of injuries include, but are not limited to, abrasion, brain injuries, bruising, burns, concussions, congestive heart failure, construction injuries, dislocation, flail chest, fracture, hemothorax, herniated disc, hip pointer, hypothermia, lacerations, pinched nerve, pneumothorax, rib fracture, sciatica, spinal cord injury, tendons ligaments fascia injury, traumatic brain injury, and whiplash. The sample may be taken before and/or after treatment of a subject with a disease or disorder. Samples may be taken before and/or after a treatment. Samples may be taken during a treatment or a treatment regime. Multiple samples may be taken from a subject to monitor the effects of the treatment over time. The sample may be taken from a subject known or suspected of having an infectious disease for which diagnostic antibodies are not available.

The sample may be taken from a subject suspected of having a disease or a disorder. The sample may be taken from a subject experiencing unexplained symptoms, such as fatigue, nausea, weight loss, aches and pains, weakness, or memory loss. The sample may be taken from a subject having explained symptoms. The sample may be taken from a subject at risk of developing a disease or disorder due to factors such as familial history, age, environmental exposure, lifestyle risk factors, or presence of other known risk factors.

The sample may be taken from an embryo, fetus, or pregnant woman. In some examples, the sample may comprise of proteins isolated from the mother's blood plasma. In some examples, proteins isolated from circulating fetal cells in the mother's blood.

Protein may be treated to remove modifications that may interfere with epitope binding. For example the protein may be glycosidase treated to remove post translational glycosylation. The protein may be treated with a reducing agent to reduce disulfide binds within the protein. The protein may be treated with a phosphatase to remove phosphate groups. Other non-limiting examples of post translational modifications that may be removed include acetate, amide groups, methyl groups, lipids, ubiquitin, myristoylation, palmitoylation, isoprenylation or prenylation (e.g. farnesol and geranylgeraniol), farnesylation, geranylgeranylation, glypiation, lipoylation, flavin moiety attachment, phosphopantetheinylation, and retinylidene Schiff base formation. Samples may also be treated to retain posttranslational protein modifications. In some examples, phosphatase inhibitors may be added to the sample. In some examples, oxidizing agents may be added to protect disulfide bonds.

Next, proteins may be denatured in full or in part. In some embodiments, proteins can be fully denatured. Proteins may be denatured by application of an external stress such as a detergent, a strong acid or base, a concentrated inorganic salt, an organic solvent (e.g., alcohol or chloroform), radiation or heat. Proteins may be denatured by addition of a denaturing buffer. Proteins may also be precipitated, lyophilized and suspended in denaturing buffer. Proteins may be denatured by heating. Methods of denaturing that are unlikely to cause chemical modifications to the proteins may be preferred.

Proteins of the sample may be treated to produce shorter polypeptides, either before or after conjugation. Remaining proteins may be partially digested with an enzyme such as ProteinaseK to generate fragments or may be left intact. In further examples the proteins may be exposed to proteases such as trypsin. Additional examples of proteases may include serine proteases, cysteine proteases, threonine proteases, aspartic proteases, glutamic proteases, metalloproteases, and asparagine peptide lyases.

In some cases it may be useful to remove extremely large and small proteins (e.g. Titin), such proteins may be removed by filtration or other appropriate methods. In some examples, extremely large proteins may include proteins that are over 400 kD, 450 kD, 500 kD, 600 kD, 650 kD, 700 kD, 750 kD, 800 kD or 850 kD. In some examples, extremely large proteins may include proteins that are over about 8,000 amino acids, about 8,500 amino acids, about 9,000 amino acis, about 9,500 amino acids, about 10,000 amino acids, about 10,500 amino acids, about 11,000 amino acids or about 15,000 amino acids. In some examples, small proteins may include proteins that are less than about 10 kD, 9 kD, 8 kD, 7 kD, 6 kD, 5 kD, 4 kD, 3 kD, 2 kD or 1 kD. In some examples, small proteins may include proteins that are less than about 50 amino acids, 45 amino acids, 40 amino acids, 35 amino acids or about 30 amino acids. Extremely large or small proteins can be removed by size exclusion chromatography. Extremely large proteins may be isolated by size exclusion chromatography, treated with proteases to produce moderately sized polypeptides and recombined with the moderately size proteins of the sample.

In some cases, proteins may be ordered by size. In some cases, proteins may be ordered by sorting proteins into microwells. In some cases, proteins may be ordered by sorting proteins into nanowells. In some cases, proteins may be ordered by running proteins through a gel such as an SDS-PAGE gel. In some cases, proteins may be ordered by other size-dependent fractionation methods. In some cases, proteins may be separated based on charge. In some cases, proteins may be separated based on hydrophobicity. In some cases, proteins may be separated based on other physical characteristics. In some cases, proteins may be separated under denaturing conditions. In some cases, proteins may be separated under non-denaturing conditions. In some cases, different fractions of fractionated proteins may be placed on different regions of the substrate. In some cases, different portions of separated proteins may be placed on different regions of the substrate. In some cases, a protein sample may be separated in an SDS-PAGE gel and transferred from the SDS-PAGE gel to the substrate such that the proteins are sorted by size in a continuum. In some cases, a protein sample may be sorted into three fractions based on size, and the three fractions may be applied to a first, second, and third region of the substrate, respectively. In some cases, proteins used in the systems and methods described herein may be sorted. In some cases, proteins used in the systems and methods described herein may not be sorted.

Proteins may be tagged, e.g. with identifiable tags, to allow for multiplexing of samples. Some non-limiting examples of identifiable tags include: fluorophores or nucleic acid barcoded base linkers. Fluorophores used may include fluorescent proteins such as GFP, YFP, RFP, eGFP, mCherry, tdtomato, FITC, Alexa Fluor 350, Alexa Fluor 405, Alexa Fluor 488, Alexa Fluor 532, Alexa Fluor 546, Alexa Fluor 555, Alexa Fluor 568, Alexa Fluor 594, Alexa Fluor 647, Alexa Fluor 680, Alexa Fluor 750, Pacific Blue, Coumarin, BODIPY FL, Pacific Green, Oregon Green, Cy3, Cy5, Pacific Orange, TRITC, Texas Red, R-Phycoerythrin, Allophcocyanin, or other fluorophores known in the art.

Any number of protein samples may be multiplexed. For example a multiplexed reaction may contain proteins from 2, 3, 4, 5, 6, 7, 8, 9, 10, 11, 12, 13, 14, 15, 16, 17, 18, 19, about 20, about 25, about 30, about 35, about 40, about 45, about 50, about 55, about 60, about 65, about 70, about 75, about 80, about 85, about 90, about 95, about 100 or more than 100 initial samples. The identifiable tags may provide a way to interrogate each protein as to its sample of origin, or may direct proteins from different samples to segregate to different areas on a solid support.

Substrate

In some embodiments, the proteins are then applied to a functionalized substrate to chemically attach proteins to the substrate. In some cases, the proteins may be attached to the substrate via biotin attachment. In some cases, the proteins may be attached to the substrate via nucleic acid attachment. In some embodiments, the proteins may be applied to an intermediate substance, where the intermediate substance is then attached to the substrate. In some cases, proteins may be conjugated to beads (e.g., gold beads) which may then be captured on a surface (e.g., a thiolated surface). In some cases, one protein may be conjugated to each bead. In some cases, proteins may be conjugated to beads (e.g., one protein per bead) and the beads may be captured on a surface (e.g. in microwells and/or nanowells).

The substrate may be any substrate capable of forming a solid support. Substrates, or solid substrates, as used herein can refer to any solid surface to which proteins can be covalently or non-covalently attached. Non-limiting examples of solid substrates include particles, beads, slides, surfaces of elements of devices, membranes, flow cells, wells, chambers, macrofluidic chambers, be flat or curved, or can have other shapes, and can be smooth or textured. In some cases, substrate surfaces may contain microwells. In some cases, substrate surfaces may contain nanowells. In some cases, substrate surfaces may contain one or more microwells in combination with one or more nanowells. In some embodiments, the substrate can be composed of glass, carbohydrates such as dextrans, plastics such as polystyrene or polypropylene, polyacrylamide, latex, silicon, metals such as gold, or cellulose, and may be further modified to allow or enhance covalent or non-covalent attachment of the oligonucleotides. For example, the substrate surface may be functionalized by modification with specific functional groups, such as maleic or succinic moieties, or derivatized by modification with a chemically reactive group, such as amino, thiol, or acrylate groups, such as by silanization. Suitable silane reagents include aminopropyltrimethoxysilane, aminopropyltriethoxysilane and 4-aminobutyltriethoxysilane. The substrate may be functionalized with N-Hydroxysuccinimide (NHS) functional groups. Glass surfaces can also be derivatized with other reactive groups, such as acrylate or epoxy, using, e.g., epoxysilane, acrylatesilane or acrylamidesilane. The substrate and process for oligonucleotide attachment are preferably stable for repeated binding, washing, imaging and eluting steps. In some examples, the substrate may be a slide or a flow cell.

An ordered array of functional groups may be created by, for example, photolithography, Dip-Pen nanolithography, nanoimprint lithography, nanosphere lithography, nanoball lithography, nanopillar arrays, nanowire lithography, scanning probe lithography, thermochemical lithography, thermal scanning probe lithography, local oxidation nanolithography, molecular self-assembly, stencil lithography, or electron-beam lithography. Functional groups in an ordered array may be located such that each functional group is less than 200 nanometers (nm), or about 200 nm, about 225 nm, about 250 nm, about 275 nm, about 300 nm, about 325 nm, about 350 nm, about 375 nm, about 400 nm, about 425 nm, about 450 nm, about 475 nm, about 500 nm, about 525 nm, about 550 nm, about 575 nm, about 600 nm, about 625 nm, about 650 nm, about 675 nm, about 700 nm, about 725 nm, about 750 nm, about 775 nm, about 800 nm, about 825 nm, about 850 nm, about 875 nm, about 900 nm, about 925 nm, about 950 nm, about 975 nm, about 1000 nm, about 1025 nm, about 1050 nm, about 1075 nm, about 1100 nm, about 1125 nm, about 1150 nm, about 1175 nm, about 1200 nm, about 1225 nm, about 1250 nm, about 1275 nm, about 1300 nm, about 1325 nm, about 1350 nm, about 1375 nm, about 1400 nm, about 1425 nm, about 1450 nm, about 1475 nm, about 1500 nm, about 1525 nm, about 1550 nm, about 1575 nm, about 1600 nm, about 1625 nm, about 1650 nm, about 1675 nm, about 1700 nm, about 1725 nm, about 1750 nm, about 1775 nm, about 1800 nm, about 1825 nm, about 1850 nm, about 1875 nm, about 1900 nm, about 1925 nm, about 1950 nm, about 1975 nm, about 2000 nm, or more than 2000 nm from any other functional group. Functional groups in a random spacing may be provided at a concentration such that functional groups are on average at least about 50 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, about 1000 nm, or more than 100 nm from any other functional group.

The substrate may be indirectly functionalized. For example, the substrate may be PEGylated and a functional group may be applied to all or a subset of the PEG molecules. Additionally, as discussed above, in some cases beads (e.g., gold beads) may be conjugated, and then the beads may be captured on a surface (e.g., a thiolated surface). In some cases, one protein may be conjugated for to each bead. In some cases, proteins may be conjugated to beads (e.g., one protein per bead) and the beads may be captured on a surface (e.g. in microwells and/or nanowells).

The substrate may be functionalized using techniques suitable for microscaled or nanoscaled structures (e.g., an ordered structure such as microwells, nanowells, micropillars, single molecular arrays, nanoballs, nanopillars, or nanowires). In some cases, a substrate may have microwells of different sizes. In some cases, microwells may be 1 micrometer (μm), may be about 2 μm, about 3 μm, about 4 μm, about 5 μm, about 6 μm, about 7 μm, about 8 μm, about 9 μm, about 10 μm, about 15 μm, about 20 μm, about 25 μm, about 30 μm, about 35 μm, about 40 μm, about 45 μm, about 50 μm, about 55 μm, about 60 μm, about 65 μm, about 70 μm, about 75 μm, about 80 μm, about 85 μm, about 90 μm, about 95 μm, about 100 μm, about 105 μm, about 110 μm, about 115 μm, about 120 μm, about 125 μm, about 130 μm, about 135 μm, about 140 μm, about 145 μm, about 150 μm, about 155 μm, about 160 μm, about 165 μm, about 170 μm, about 175 μm, about 180 μm, about 185 μm, about 190 μm, about 195 μm, about 200 μm, about 205 μm, about 210 μm, about 215 μm, about 220 μm, about 225 μm, about 230 μm, about 235 μm, about 240 μm, about 245 μm, about 250 μm, about 255 μm, about 260 μm, about 265 μm, about 270 μm, about 275 μm, about 280 μm, about 285 μm, about 290 μm, about 295 μm, about 300 μm, about 305 μm, about 310 μm, about 315 μm, about 320 μm, about 325 μm, about 330 μm, about 335 µm, about 340 µm, about 345 µm, about 350 µm, about 355 µm, about 360 µm, about 365 µm, about 370 µm, about 375 µm, about 380 µm, about 385 µm, about 390 µm, about 395 µm, about 400 µm, about 405 µm, about 410 µm, about 415 µm, about 420 µm, about 425 µm, about 430 µm, about 435 µm, about 440 µm, about 445 µm, about 450 µm, about 455 µm, about 460 µm, about 465 µm, about 470 µm, about 475 µm, about 480 µm, about 485 µm, about 490 µm, about 495 µm, about 500 or more than 500 µm. In some cases, a substrate may have microwells that range in size from 5 µm to 500 µm In some cases, a substrate may have microwells that range in size from about 5 µm to about 500 µm. In some cases, a substrate may have microwells that range in size from 10 µm to 100 µm. In some cases, a substrate may have microwells that range in size from about 10 µm to about 100 In some cases, a substrate may have a range of different sized microwells such that proteins of different sizes may be sorted into different sized microwells. In some cases, microwells in the substrate may be distributed by size (e.g. with larger microwells distributed in a first region and with smaller microwells distributed in a second region). In some cases, a substrate may have microwells of about ten different sizes. In some cases, a substrate may have microwells of about 20 different sizes, about 25 different sizes, about 30 different sizes, about 35 different sizes, about 40 different sizes, about 45 different sizes, about 50 different sizes, about 55 different sizes, about 60 different sizes, about 65 different sizes, about 70 different sizes, about 75 different sizes, about 80 different sizes, about 85 different sizes, about 90 different sizes, about 95 different sizes, about 100 different sizes, or more than 100 different sizes.

In some cases, a substrate may have nanowells of different sizes. In some cases, nanowells may be about 100 nanometers (nm), about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, or between 950 nm and 1 micrometer. In some cases, a substrate may have nanowells that range in size from 100 nm to 1 micrometer. In some cases, a substrate may have nanowells that range in size from 100 nm to 500 nm. In some cases, a substrate may have a range of different sized nanowells such that proteins of different sizes may be sorted into different sized nanowells. In some cases, nanowells in the substrate may be distributed by size (e.g. with larger nanowells distributed in a first region and with smaller nanowells distributed in a second region). In some cases, a substrate may have nanowells of about ten different sizes. In some cases, a substrate may have nanowells of about 20 different sizes, or more than 30 different sizes.

In some cases, a substrate may have a range of different sized nanowells and/or microwells such that proteins of different sizes may be sorted into different sized nanowells and/or microwells. In some cases, nanowells and/or microwells in the substrate may be distributed by size (e.g. with larger microwells distributed in a first region and with smaller microwells distributed in a second region). In some cases, a substrate may have nanowells and/or microwells of about ten different sizes. In some cases, a substrate may have nanowells and/or microwells of about 20 different sizes, about 25 different sizes, about 30 different sizes, about 35 different sizes, about 40 different sizes, about 45 different sizes, about 50 different sizes, about 55 different sizes, about 60 different sizes, about 65 different sizes, about 70 different sizes, about 75 different sizes, about 80 different sizes, about 85 different sizes, about 90 different sizes, about 95 different sizes, about 100 different sizes, or more than 100 different sizes.

The substrate may comprise any material, including metals, glass, plastics, ceramics or combinations thereof. In some preferred embodiments, the solid substrate can be a flow cell. The flow cell can be composed of a single layer or multiple layers. For example, a flow cell can comprise a base layer (e.g., of boro silicate glass), a channel layer (e.g., of etched silicon) overlaid upon the base layer, and a cover, or top, layer. When the layers are assembled together, enclosed channels can be formed having inlet/outlets at either end through the cover. The thickness of each layer can vary, but is preferably less than about 1700µm. Layers can be composed of any suitable material known in the art, including but not limited to photosensitive glasses, borosilicate glass, fused silicate, PDMS or silicon. Different layers can be composed of the same material or different materials.

In some embodiments, flow cells can comprise openings for channels on the bottom of the flow cell. A flow cell can comprise millions of attached target conjugation sites in locations that can be discretely visualized. In some embodiments, various flow cells of use with embodiments of the invention can comprise different numbers of channels (e.g., 1 channel, 2 or more channels, 3 or more channels, 4 or more channels, 6 or more channels, 8 or more channels, 10 or more channels, 12 or more channels, 16 or more channels, or more than 16 channels). Various flow cells can comprise channels of different depths or widths, which may be different between channels within a single flow cell, or different between channels of different flow cells. A single channel can also vary in depth and/or width. For example, a channel can be less than about 50µm deep, about 50µm deep, less than about 100µm deep, about 100µm deep, about 100µm ío about 500µm deep, about 500µm deep, or more than about 500µm deep at one or more points within the channel. Channels can have any cross sectional shape, including but not limited to a circular, a semi-circular, a rectangular, a trapezoidal, a triangular, or an ovoid cross-section.

The proteins may be spotted, dropped, pipetted, flowed, washed or otherwise applied to the substrate. In the case of a substrate that has been functionalized with a moiety such as an NHS ester, no modification of the protein is required. In the case of a substrate that has been functionalized with alternate moieties (e.g. a sulfhydryl, amine, or linker nucleic acid), a crosslinking reagent (e.g. disuccinimidyl suberate, NHS, sulphonamides) may be used. In the case of a substrate that has been functionalized with linker nucleic acid the proteins of the sample may be modified with complementary nucleic acid tags.

In some cases, a protein may be conjugated to a nucleic acid. Using the nucleic acid, a nucleic acid nanoball may be formed, thereby having the protein linked to the nucleic acid nanoball. When the nucleic acid nanoball is attached to a substrate, the protein attached to the nucleic acid is attached to the substrate by way of the nucleic acid nanoball. A DNA nanoball can be attached (e.g. by adsorption or by conjugation) to a substrate. The substrate may have an amine functionalized surface to which the nucleic acid nanoballs can attach.

In some cases, a nucleic acid nanoball may be formed with a functionally active terminus (e.g. a maleimide, NETS-Ester, etc.). The protein may then be conjugated to the nanoball thereby having the protein linked to the nucleic acid nanoball. When the nucleic acid nanoball is attached to a substrate, the protein attached to the nucleic acid is attached to the substrate by way of the nucleic acid nanoball. A DNA nanoball can be attached (e.g. by adsorption or by conjugation) to a substrate. The substrate may have an amine functionalized surface to which the nucleic acid nanoballs can attach.

Photo-activatable cross linkers may be used to direct cross linking of a sample to a specific area on the substrate. Photo-activatable cross linkers may be used to allow multiplexing of protein samples by attaching each sample in a known region of the substrate. Photo-activatable cross linkers may allow the specific attachment of proteins which have been successfully tagged, for example by detecting a fluorescent tag before cross linking a protein. Examples of photo-activatable cross linkers include, but are not limited to, N-5-azido-2-nitrobenzoyloxysuccinimide, sulfosuccinimidyl 6-(4'-azido-2'-nitrophenylamino)hexanoate, succinimidyl 4,4'-azipentanoate, sulfosuccinimidyl 4,4'-azipentanoate, succinimidyl 6-(4,4'-azipentanamido)hexanoate, sulfosuccinimidyl 6-(4,4'-azipentanamido)hexanoate, succinimidyl 2-((4,4'-azipentanamido)ethyl)-1,3'-dithiopropionate, and sulfosuccinimidyl 2-((4,4'-azipentanamido)ethyl)-1,3'-dithiopropionate.

Samples may also be multiplexed by restricting the binding of each sample to a discrete area on the substrate. For example the substrate may be organized into lanes. Another method for multiplexing is to apply the samples iteratively across the substrate, following each sample application with a protein detection step utilizing a nonspecific protein binding reagent or dye. In some cases, examples of dyes may include fluorescent protein gel stains such as SYPRO® Ruby, SYPRO® Orange, SYPRO® Red, SYPRO® Tangerine, and Coomassie™ Fluor Orange.

By tracking the locations of all proteins after each addition of sample it is possible to determine the stage at which each location on the substrate first contained a protein, and thus from which sample that protein was derived. This method may also determine the saturation of the substrate after each application of sample and allows for maximization of protein binding on the substrate. For example if only 30% of functionalized locations are occupied by protein after a first application of a sample then either a second application of the same sample or an application of a different sample may be made.

The polypeptides may be attached to the substrate by one or more residues. In some examples, the polypeptides may be attached via the N terminal, C terminal, both terminals, or via an internal residue.

In addition to permanent crosslinkers, it may be appropriate for some applications to use photo-cleavable linkers and that doing so enables proteins to be selectively extracted from the substrate following analysis. In some cases photo-cleavable cross linkers may be used for several different multiplexed samples. In some cases photo-cleavable cross linkers may be used from one or more samples within a multiplexed reaction. In some cases a multiplexed reaction may comprise control samples cross linked to the substrate via permanent crosslinkers and experimental samples cross linked to the substrate via photo-cleavable crosslinkers.

Each conjugated protein may be spatially separated from each other conjugated protein such that each conjugated protein is optically resolvable. Proteins may thus be individually labeled with a unique spatial address. In some embodiments, this can be accomplished by conjugation using low concentrations of protein and low density of attachment sites on the substrate so that each protein molecule is spatially separated from each other protein molecule. In examples where photo-activatable crosslinkers are used, a light pattern may be used such that proteins are affixed to predetermined locations.

In some methods, bulk proteins that have been purified may be conjugated to a substrate and processed using methods described herein so as to identify the purified protein. Bulk proteins may comprise purified proteins that have been collected together. In some examples, bulk proteins may be conjugated at a location that is spatially separated from each other conjugated protein or bulk proteins such that each conjugated protein or bulk protein is optically resolvable. Proteins, or bulk proteins, may thus be individually labeled with a unique spatial address. In some embodiments, this can be accomplished by conjugation using low concentrations of protein and low density of attachment sites on the substrate so that each protein molecule is spatially separated from each other protein molecule. In examples where photo-activatable crosslinkers are used, a light pattern may be used such that one or more proteins are affixed to predetermined locations.

In some embodiments, each protein may be associated with a unique spatial address. For example, once the proteins are attached to the substrate in spatially separated locations, each protein can be assigned an indexed address, such as by coordinates. In some examples, a grid of pre-assigned unique spatial addresses may be predetermined. In some embodiments the substrate may contain easily identifiable fixed marks such that placement of each protein can be determined relative to the fixed marks of the substrate. In some examples the substrate may have grid lines and/or and "origin" or other fiducials permanently marked on the surface. In some examples the surface of the substrate may be permanently or semi-permanently marked to provide a reference by which to locate cross linked proteins. The shape of the patterning itself, such as the exterior border of the conjugated polypeptides may also be used as fiducials for determining the unique location of each spot.

The substrate may also contain conjugated protein standards and controls. Conjugated protein standards and controls may be peptides or proteins of known sequence which have been conjugated in known locations. In some examples, conjugated protein standards and controls may serve as internal controls in an assay. The proteins may be applied to the substrate from purified protein stocks, or may be synthesized on the substrate through a process such as Nucleic Acid-Programmable Protein Array (NAPPA).

In some examples, the substrate may comprise fluorescent standards. These fluorescent standards may be used to calibrate the intensity of the fluorescent signals from assay to assay. These fluorescent standards may also be used to correlate the intensity of a fluorescent signal with the number of fluorophores present in an area. Fluorescent standards may comprise some or all of the different types of fluorphores used in the assay.

Affinity Reagents

Once the substrate has been conjugated with the proteins from the sample, multi-affinity reagent measurements can be performed. The measurement processes described herein may utilize various affinity reagents.

Affinity reagents may be any reagents which bind proteins or peptides with reproducible specificity. For example the affinity reagents may be antibodies, antibody fragments, aptamers, or peptides. In some examples, monoclonal antibodies may be preferred. In some examples, antibody fragments such as Fab fragments may be preferred. In some cases the affinity reagents may be commercially available affinity reagents, such as commercially available antibodies. In some cases the desired affinity reagents may be selected by screening commercially available affinity reagents to identify those with useful characteristics. In some cases, affinity reagents may be screened for their ability to bind a single protein. In some cases, affinity reagents may be screened for their ability to bind an epitope or amino-acid sequence. In some cases, groups of affinity reagents may be screened for their ability to collectively resolve similar proteins (e.g those with highly similar sequence) through differential binding. In some cases, affinity reagents may be screened for to have overlapping binding characteristics to increase binding specificity for a particular protein. Screening of affinity reagents may be performed in a variety of different ways. One example would be to screen affinity reagents against a NAPPA or an epitope tiling array. In some cases, protein-specific affinity reagents designed to bind to a protein target may be used (e.g. commercially available antibodies or aptamers). In some cases, multiple protein-specific affinity reagents may be mixed prior to binding measurement. For example, for each binding measurement pass, a new mixture of protein specific affinity reagents may be selected comprising a subset of the available affinity reagents selected at random from the complete set. For example, each subsequent mixture may be generated in the same random manner, with the expectation that many of the affinity reagents will be present in more than one of the mixtures. In some cases, protein identifications may be generated more rapidly using mixtures of protein-specific affinity reagents. In some cases, such mixtures of protein-specific affinity reagents may increase the percentage of unknown proteins for which an affinity reagent binds in any individual pass. Mixtures of affinity reagents may consist of 1%, 5%, 10%, 20%, 30%, 40%, 50%, 60%, 70%, 80%, 90% or more of all available affinity reagents.

The affinity reagents may have high, moderate or low specificity. In some examples the affinity reagents may recognize several different epitopes. In some examples the affinity reagents may recognize epitopes present in two or more different proteins. In some examples the affinity reagents may recognize epitopes present in many different proteins. In some cases an affinity reagent used in the methods of this disclosure may be highly specific for a single epitope. In some cases an affinity reagent used in the methods of this disclosure may be highly specific for a single epitope containing a posttranslational modification.

In some embodiments, an affinity reagent that is directed towards identifying a target amino acid sequence may actually comprise a group of different components which are not differentiated or distinguishable from each other as used in methods described herein. In particular, the different components that may be used to identify the same target amino acid sequence may use the same detection moiety to identify the same target amino acid sequence. For example, an affinity reagent which binds a trimer amino acid sequence (AAA) regardless of flanking sequences may comprise either a single probe which binds the trimer AAA sequence without any effect from flanking sequences, or a group of 400 probes, each of which binds to a different 5 amino acid epitope of the form $\alpha AAA\beta$, where $\alpha$ and $\beta$ may be any amino acid. In the some cases of the second case, the 400 probes may be combined such that there is an equal amount of each one. In some cases of the second case, the 400 probes may be combined such that the amounts of each probe may be weighted by the characteristic binding affinities of each probe such that there is an equal probability of any given 5 amino acid epitope being bound.

Novel affinity reagents may be generated by any method known in the art. Methods of developing affinity reagents include SELEX, phage display, and inoculation. In some examples affinity reagents may be designed using structure based drug design methods. Structure-based drug design (or direct drug design) utilizes knowledge of the three dimensional structure of the epitope of interest and the binding site of the affinity reagent.

In some cases the affinity reagents may be labeled with nucleic acid barcodes. In some examples, nucleic acid barcodes may be used to purify affinity reagents after use. In some examples, nucleic acid barcodes may be used to sort the affinity reagents for repeated uses. In some cases the affinity reagents may be labeled with fluorophores which may be used to sort the affinity reagents after use.

In some cases, multiple affinity reagents that are labeled with nucleic acid barcodes may be multiplexed and then detected using complementary nucleic acid probes. A multiplexed group of affinity reagents may be detected in a single cycle using multiple complementary nucleic acids with distinct detection moieties. In some cases, a multiplexed group of affinity reagents may be detected in multiple cycles using a single complementary nucleic acid conjugated to a detection moiety. In some cases, a multiplexed group of affinity reagents may be detected in multiple cycles using multiple complementary nucleic acids each conjugated to a distinct detection moiety. In some cases, a multiplexed group of affinity reagents may be detected in multiple cycles using multiple complementary nucleic acids each conjugated to a distinct group detection moieties.

In some cases, one or more affinity reagents, that are labeled with nucleic acid barcodes, may be cross-linked to a bound protein. Once the one or more affinity reagents are cross-linked to the protein, the barcodes may be sequenced to determine the identity of the cross-linked affinity reagent. In some cases, multiple bound proteins may be exposed to the one or more affinity reagents. In some cases, when multiple bound proteins are cross-linked with one or more affinity reagents, the barcodes associated with the bound affinity reagents may be sequenced to determine the identity of the cross-linked affinity reagents associated with each of the multiple bound proteins.

The family of affinity reagents may comprise one or more types of affinity reagents. For example the methods of the present disclosure may use a family of affinity reagents comprising one or more of antibodies, antibody fragments, Fab fragments, aptamers, peptides, and proteins.

The affinity reagents may be modified. Modifications include, but are not limited to, attachment of a detection moiety. Detection moieties may be directly or indirectly attached. For example the detection moiety may be directly covalently attached to the affinity reagent, or may be attached through a linker, or may be attached through an affinity reaction such as complementary nucleic acid tags or a biotin streptavidin pair. Attachment methods that are able to withstand gentle washing and elution of the affinity reagent may be preferred.

Detection moieties include, but are not limited to, fluorophores, bioluminescent proteins, nucleic acid segments including a constant region and barcode region, or chemical tethers for linking to a nanoparticle such as a magnetic particle. Detection moieties may include several different flurophores with different patterns of excitation or emission.

The detection moiety may be cleavable from the affinity reagent. This can allow for a step in which the detection moieties are removed from affinity reagents that are no longer of interest to reduce signal contamination.

In some cases the affinity reagents are unmodified. For example if the affinity reagent is an antibody then the presence of the antibody may be detected by atomic force microscopy. The affinity reagents may be unmodified and may be detected, for example, by having antibodies specific to one or more of the affinity reagents. For example if the affinity reagent is a mouse antibody then the mouse antibody may be detected by using an anti-mouse secondary antibody. Alternately the affinity reagent may be an aptamer which is detected by an antibody specific for the aptamer. The secondary antibody may be modified with a detection moiety as described above. In some cases the presence of the secondary antibody may be detected by atomic force microscopy.

In some examples, the affinity reagents may comprise the same modification, for example a conjugated green fluorescent protein, or may comprise two or more different types of modification. For example, each affinity reagent may be conjugated to one of several different fluorescent moieties, each with a different wavelength of excitation or emission. This may allow multiplexing of the affinity reagents as several different affinity reagents may be combined and/or distinguished. In one example, a first affinity reagent may be conjugated to a green fluorescent protein, a second affinity reagent may be conjugated to a yellow fluorescent protein and a third affinity reagent may be conjugated to a red fluorescent protein, thus the three affinity reagents can be multiplexed and identified by their fluorescence. In a further example a first, fourth and seventh affinity reagent may be conjugated to a green fluorescent protein, a second, fifth and eighth affinity reagent may be conjugated to a yellow fluorescent protein and a third, sixth and ninth affinity reagent may be conjugated to a red fluorescent protein; in this case the first, second and third affinity reagents may be multiplexed together while the second, fourth and seventh, and third, sixth and ninth affinity reagents form two further multiplexing reactions. The number of affinity reagents which can be multiplexed together may depend on the detection moieties used to differentiate them. For example, the multiplexing of affinity reagents labeled with fluorophores may be limited by the number of unique fluorophores available. For further example, the multiplexing of affinity reagents labeled with nucleic acid tags may be determined by the length of the nucleic acid bar code.

The specificity of each affinity reagent can be determined prior to use in an assay. The binding specificity of the affinity reagents can be determined in a control experiment using known proteins. Any appropriate experimental methods may be used to determine the specificity of the affinity reagent. In one example a substrate may be loaded with known protein standards at known locations and used to assess the specificity of a plurality of affinity reagents. In another example, a substrate may contain both experimental samples and a panel of controls and standards such that the specificity of each affinity reagent can be calculated from the binding to the controls and standards and then used to identify the experimental samples. In some cases affinity reagents with unknown specificity may be included along with affinity reagents of known specificity, data from the known specificity affinity reagents may be used to identify proteins, and the pattern of binding of the unknown specificity affinity reagents to the identified proteins may be used to determine their binding specificity. It is also possible to reconfirm the specificity of any individual affinity reagent by using the known binding data of other affinity reagents to assess which proteins the individual affinity reagent bound. Thus with multiple uses of an affinity reagent panel the specificities of the affinity reagents may be increasingly refined with each iteration. While affinity reagents that are uniquely specific to particular proteins may be used, methods described herein may not require them. Additionally, methods may be effective on a range of specificities. In some examples, methods described herein may be particularly efficient when affinity reagents are not specific to any particular protein, but are instead specific to amino acid motifs (e.g. the tri-peptide AAA).

In some examples, one or more affinity reagents may be chosen to bind amino acid motifs of a given length, such as 2, 3, 4, 5, 6, 7, 8, 9, 10, or more than 10 amino acids. In some examples, one or more affinity reagents may be chosen to bind amino acid motifs of a range of different lengths from 2 amino acids to 40 amino acids.

In some examples, the affinity reagents may be chosen to have high, moderate, or low binding affinities. In some cases affinity reagents with low or moderate binding affinities may be preferred. In some cases the affinity reagents may have dissociation constants of about $10^{-3}$ M, $10^{-4}$ M, $10^{-5}$M, $10^{-6}$ M, $10^{-7}$M, $10^{-8}$M, $10^{-9}$ M, $10^{-10}$ M or lower. In some cases the affinity reagents may have dissociation constants of greater than about $10^{-10}$ M, $10^{-9}$M, $10^{-8}$ M, $10^{-7}$M, $10^{-6}$ M, $10^{-5}$M, $10^{-4}$ M, $10^{-3}$ M, $10^{-2}$ M or higher.

Some of the affinity reagents may be chosen to bind modified amino acid sequences, such as phosphorylated or ubiquinated amino acid sequences. In some examples, one or more affinity reagents may be chosen to be broadly specific for a family of epitopes that may be contained by one or more proteins. In some examples, one or more affinity reagents may bind two or more different proteins. In some examples, one or more affinity reagents may bind weakly to their target or targets. For example, affinity reagents may bind less than 10%, less than 10%, less than 15%, less than 20%, less than 25%, less than 30%, less than 35%, or less than 35% to their target or targets. In some examples, one or more affinity reagents may bind moderately or strongly to their target or targets. For example, affinity reagents may bind more than 35%, more than 40%, more than 45%, more than 60%, more than 65%, more than 70%, more than 75%, more than 80%, more than 85%, more than 90%, more than 91%, more than 92%, more than 93%, more than 94%, more than 95%, more than 96%, more than 97%, more than 98%, or more than 99% to their target or targets.

To compensate for weak binding, an excess of the affinity reagent may be applied to the substrate. The affinity reagent may be applied at about a 1:1, 2:1, 3:1, 4:1, 5:1, 6:1, 7:1, 8:1, 9:1 or 10:1 excess relative to the sample proteins. The affinity reagent may be applied at about a 1:1, 2:1, 3:1, 4:1, 5:1, 6:1, 7:1, 8:1, 9:1 or 10:1 excess relative to the expected incidence of the epitope in the sample proteins.

The affinity reagents may also comprise a magnetic component. The magnetic component may be useful for manipulating some or all bound affinity reagents into the same imaging plane or z stack. Manipulating some or all affinity reagents into the same imaging plane may improve the quality of the imaging data and reduce noise in the system.

Binding Measurements

Given a set of modified affinity reagents and a conjugated substrate, affinity reagents may be iteratively applied to the substrate. Each measurement cycle consists of several stages. In the first stage, affinity reagents are applied to the substrate where they may adsorb to the conjugated proteins.

Next, the substrate can be lightly washed to remove non-specific binding. This washing step can be performed under conditions which will not elute affinity reagents which have bound to the immobilized proteins. Some examples of buffers which could be used for this step include phosphate buffered saline, Tris buffered saline, phosphate buffered saline with Tween20, and Tris buffered saline with Tween20.

Following adsorption, the binding addresses for each modified affinity reagent are determined, such as through measurement of a fluorophore that has been conjugated to the affinity reagents directly, or to a complement nucleic acid to a nucleic acid strand conjugated to the affinity reagents. The detection method is determined by the choice of detection moiety. Fluorophores and bioluminescent moieties may be optically detected, in some cases secondary detection reagents are required. The unique address of each immobilized protein on the substrate may be determined prior to the binding measurements, or a list of addresses containing immobilized proteins may be generated through the binding measurements.

Next, the affinity reagents can be desorbed through a more stringent wash. This wash step may remove some or all affinity reagents from the immobilized substrates. In some cases affinity reagents may have been chosen to have low to moderate binding affinities to facilitate removal. Used affinity reagents may be re-captured for reuse or discarded. In examples where affinity reagents with cleavable detection moieties are used, the detection moieties may be cleaved and removed at this stage. Following stringent washing, in some examples, any remaining fluorescence can be quenched and even more stringent washing applied to remove leftover affinity reagent. Carry-over/contamination can be detected by reimaging the substrate before applying the next affinity reagent. Contamination may also be detected by monitoring consecutive for images for recurring signals. This concludes one cycle of analysis.

In some embodiments the fluorescently tagged affinity reagents may be quenched by exposure to prolonged intense light at the activation wavelength. Quenching of the fluorescent tags may replace washing steps to remove the affinity reagents. In some embodiments, it may be desirable to cycle n fluorophores to distinguish which signals were derived from the previous n-1 cycles.

Figure 10:
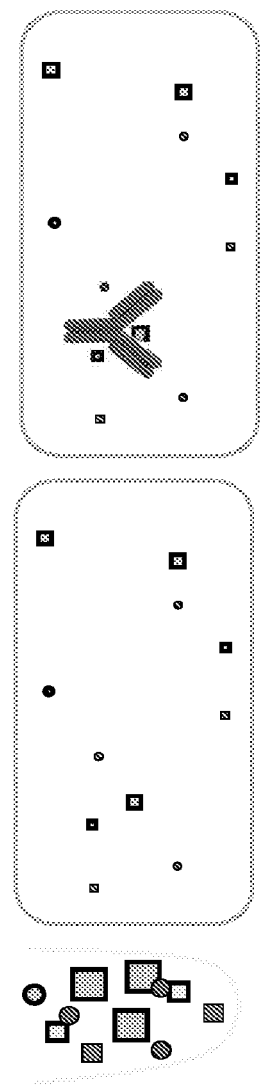
FIG. 10 illustrates computational decoding of antibody measurement data, in accordance with some embodiments.

Cycles continue for each affinity reagent, or multiplexing thereof. The result of the measurement phase is a very large table listing the binding coordinates for each affinity reagent, or the affinity reagents which bound at each coordinated location, see for example FIG. 10.

Analysis

The last step in protein identification may comprise a software tool to determine the most likely identity of each protein at each coordinate of the substrate from the information about which affinity reagents bound to that coordinate. The software may utilize information about the binding characteristics of each affinity reagent. For example, if a given affinity reagent preferentially binds to proteins containing the tri-peptide epitope AAA. Given the information about the binding characteristic of each affinity reagent, a database of the proteins in the sample, and list of binding coordinates, the pattern of binding, the software tool assigns a probable identity to each coordinate as well as a confidence for that identity. In the extreme case of precise 1-1 mappings between affinity reagents and proteins, this can be accomplished with a simple lookup table. However, in the case where binding is more complex, this may be performed via solving the appropriate satisfaction problem. In cases where the binding characteristics are highly complex, an expectation maximization approach may be employed.

The software could also utilize a listing of some or all locations in which each affinity reagent did not bind and use this information about the absence of epitopes to determine the protein present. The software could also utilize information about which affinity reagents did and did not bind to each address. Thus the software would use the information about both which epitopes were present and which epitopes were not present. The software may comprise a database. The database may contain sequences of some or all known proteins in the species from which the sample was obtained. For example if the sample is known to be of human origin then a database with the sequences of some or all human proteins may be used. If the species of the sample is unknown then a database of some or all protein sequences may be used. The database may also contain the sequences of some or all known protein variants and mutant proteins, and the sequences of some or all possible proteins that could result from DNA frameshift mutations. The database may also contain sequences of possible truncated proteins that may arise from premature stop codons, or from degradation.

The software may comprise one or more algorithms, such as a machine learning, deep learning, statistical learning, supervised learning, unsupervised learning, clustering, expectation maximization, maximum likelihood estimation, Bayesian inference, linear regression, logistic regression, binary classification, multinomial classification, or other pattern recognition algorithm. For example, the software may perform the one or more algorithms to analyze the information (e.g., as inputs of the one or more algorithm) of (i) the binding characteristic of each affinity reagent, (ii) the database of the proteins in the sample, (iii) the list of binding coordinates, and/or (iv) the pattern of binding of affinity reagents to proteins, in order to generate or assign (e.g., as outputs of the one or more algorithms) (a) a probable identity to each coordinate and/or (b) a confidence (e.g., confidence level and/or confidence interval) for that identity. Examples of machine learning algorithms may include support vector machines (SVMs), neural networks, convolutional neural networks (CNNs), deep neural networks, cascading neural networks, k-Nearest Neighbor (k-NN) classification, random forests (RFs), and other types of classification and regression trees (CARTs).

The software may be trained by performing the methods of this disclosure on a substrate where the identity of the protein at each address is predetermined. For example the software may be trained using a Nucleic Acid-Programmable Protein Array or epitope tiling array as a training dataset.

Determining Characteristics of Sample

Once decoding is complete, the probable identities of the proteins conjugated to each address are defined. Consequently, their abundance in the mixture can be estimated by counting observations. Thus a listing of each protein present in the mixture, and the number of observances of that protein can be compiled.

Further, if a photo-cleavable linker, or other form of specifically cleavable linker, is used to attach the proteins to the substrate then specific proteins of interest may be released from the substrate and collected for further study. For example specific proteins may be identified and eluted for further study. The methods of this disclosure may also serve as a way to purify and/or isolate a desired protein from a mixture. In some cases the method may be able to purify and/or isolate specific isotypes or post translationally modified proteins. In samples for which a complete list of possible proteins and associated sequences is not available this method may be able to distinguish different proteins of distinguish groups of proteins, these could then be eluted for further study. For example, for highly complex samples containing many unknown proteins, such as gut microbiome samples, the methods described herein may be used to fractionate the sample prior to mass spectrometry. In some cases proteins may be eluted from the substrate once their identities can be called. Removing the proteins from the substrate as they are identified allows subsequent rounds of affinity reagent binding to continue for the proteins whose identities cannot yet be called, and may decrease background noise and off target signals for the remaining rounds. In some examples one or more affinity reagents with specificity to particular proteins may be used as a first round to identify high abundance proteins such as serum albumin or immunoglobulins in a blood sample, these high abundance proteins may then be removed early in the process. In some cases a subset of the proteins on the substrate may be removed after every round of affinity reagent binding, or after every second, third, fourth, fifth, sixth, seventh, eighth, ninth, tenth, fifteenth, twentieth or more than twentieth round of affinity reagent binding. The signal to noise ratio may increase after each round of protein elution.

In some cases, unidentified proteins may be grouped or clustered based on their binding patterns. For example, in some cases, proteins present in the sample may not be represented in the sequence database. Unidentified proteins may be clustered into groups based on their binding patterns to the affinity probes with the goal of each group containing a set of unknown proteins in the sample with the same sequence. Protein quantities may be estimated for each group and included in quantitative analyses including, but not limited to, differential quantification between healthy and disease states, longitudinal analysis, or biomarker discovery. In some cases, an unidentified group may be selectively removed from the substrate for identification by mass spectrometry. In other cases, the unidentified group may be identified by performing further binding affinity measurement experiments specifically designed to generate confident identification.

In some cases after a protein or set of proteins have been removed it may be possible to add additional sample to the substrate. For example serum albumin is a high abundance protein in blood serum which may account for about half the protein in a sample, removing serum albumin after a first round of affinity reagent binding may allow the addition of further blood sample to the substrate. In some embodiments it may be preferred to remove high abundance proteins prior to immobilizing a sample on a substrate, for example through immunoprecipitation or affinity column purification.

Protein modifications may be identified using the methods of this disclosure. For example, post translational modifications may be identified by iterative cycles of detection using modification specific detection reagents interspersed with enzymatic processing (for example phosphatase treatment). Affinity reagents specific for different modifications may be used to determine the presence of absence of such modifications on the immobilized proteins. The method also allows quantification of the number of instances of each protein with and without a given modification.

Mutations in proteins may be detected by matching inconsistencies between the binding pattern of a sample protein and the predicted protein identity. For example an immobilized protein or polypeptide on the substrate which matches the affinity reagent binding profile of a known protein except for the binding of one affinity reagent may have an amino acid substitution. As affinity reagents may have overlapping epitopes an immobilized protein may have several mismatches from the predicted affinity binding pattern despite having a single amino acid substitution. DNA mutations which cause frameshifts of premature stop codons may also be detected.

Figure 13:
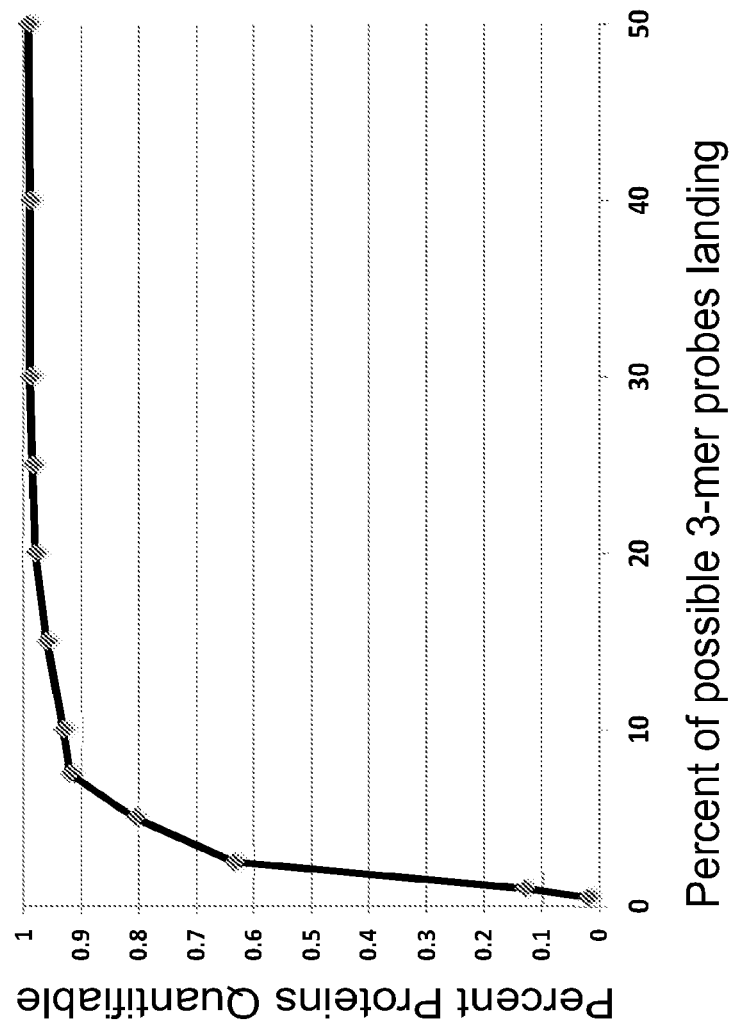
FIG. 13 illustrates coverage of 3-mer d-code antibody sampling that may be required for quantification, in accordance with embodiments.

The number of affinity reagents required may be less than the total number of epitopes present in the sample. For example if the affinity reagents are selected such that each affinity reagent recognizes one unique three peptide epitope then the total set of affinity reagents to recognize all possible epitopes in the sample is 20×20×20=8000. However the methods of the present disclosure may only require about 100, 200, 300, 400, 500, 600, 700, 800, 900, 1000, 1500, 2000, 2500, 3000, 3500, 4000, 4500, 5000, 5500 or 6000 of these affinity reagents. In some cases the methods may only require less than about 500, 1000, 2500, 3000, 3500, 4000, 4500, 5000, 5500 or 6000 affinity reagents. FIG. 13 shows the results of a simulation demonstrating the percentage of known human proteins that can be identified given a set of x affinity reagents specific to unique amino acid 3-mers as a function of the binding efficiency of each affinity reagent. As seen in FIG. 13, 98% of human proteins can be uniquely identified with 8000 3-mer affinity reagents, and a binding likelihood of 10%.

The methods of the present disclosure may be highly accurate. The methods of the present disclosure may be able to identify each protein with about 90%, 91%, 92%, 93%, 94%, 95%, 96%, 97%, 98%, 98.5%, 99%, 99.5% 99.9% or more than 99.9% accuracy.

The methods of the present disclosure may be able to predict the identity of each protein with about 90%, 91%, 92%, 93%, 94%, 95%, 96%, 97%, 98%, 98.5%, 99%, 99.5% 99.9% or more than 99.9% confidence. The degree of confidence may be different for different proteins within the sample. For example proteins with very unique sequences may be identified with higher confidence than proteins which are highly similar to other proteins. In some cases a protein may be identified as part of a family of proteins with high confidence, however the exact identity of the protein may be predicted with lower confidence. In some cases proteins that are extremely large or extremely small may be predicted with lower confidence than proteins of more moderate size.

In some cases a protein may be identified as part of a family of proteins with high confidence, however the exact identity of the protein may be predicted with lower confidence. For example, a protein containing a single amino acid variant may be difficult to resolve from the canonical form of the protein with high confidence. In this case, neither the canonical sequence nor the single amino acid variant-containing form may have high confidence, but a high confidence can be assessed to the unknown protein being part of the group of proteins containing both sequences. A similar case may occur in instances where a protein may have multiple related isoforms with similar sequence.

The methods of the present disclosure may be able to identify some or all proteins in a given sample. The methods of the present disclosure maybe able to identify about 90%, 91%, 92%, 93%, 94%, 95%, 96%, 97%, 98%, 98.5%, 99%, 99.5% 99.9% or more than 99.9% of proteins in a sample.

The methods of the present disclosure may be able to rapidly identify proteins in a sample. The methods of the present disclosure may be able to identify more than about 100, about 1000, about 5000, about 10000, about 20,000, about 30,000, about 40,000, about 50,000, about 100,000, 1,000,000, about 10,000,000, about 100,000,000, about 1,000,000,000, about 10,000,000,000, about 100,000,000,000, about 1,000,000,000,000 proteins per flowcell per day. The methods of the present disclosure may be able to identify more than about $10^{10}$, $10^{11}$, $10^{12}$, $10^{13}$, $10^{14}$, $10^{15}$, $10^{16}$, $10^{17}$, or more than about $10^{17}$ proteins per flowcell per day. The methods of the present disclosure may be able to identify about $10^{10}$-$10^{12}$, $10^{11}$-$10^{14}$, $10^{12}$-$10^{16}$, or $10^{13}$-$10^{17}$ proteins per flowcell per day. The methods of the present disclosure may be able to identify more than 95% of the proteins within about 10 pg, about 20 pg, about 30 pg, about 40 pg, about 50 pg, about 60 pg, about 70 pg, about 80 pg, about 90 pg, about 100 pg, about 300 pg, about 300 pg, about 400 pg, about 500 pg, about 600 pg, about 700 pg, about 800 pg, about 900 pg, about 1 ng, about 2 ng, about 3 ng, about 4 ng, about 5 ng, about 6 ng, about 7 ng, about 8 ng, about 8 ng, about 10 ng, about 10 ng, about 20 ng, about 30 ng, about 40 ng, about 50 ng, about 60 ng, about 70 ng, about 80 ng, about 90 ng, about 100 ng, about 300 ng, about 300 ng, about 400 ng, about 500 ng, about 600 ng, about 700 ng, about 800 ng, about 900 ng, about 1 μg, about 2 μg, about 3 μg, about 4 μg, about 5 μg, about 6 μg, about 7 μg, about 8 μg, about 8 μg, about 10 μg, about 10 μg, about 20 μg, about 30 μg, about 40 μg, about 50 μg, about 60 μg, about 70 μg, about 80 μg, about 90 μg, about 100 μg, about 300 μg, about 300 μg, about 400 μg, about 500 μg, about 600 μg, about 700 μg, about 800 μg, about 900 μg, or more than about 1 mg of protein per flowcell per day.

The methods of the present disclosure may be used to assess the proteome after an experimental treatment. The methods of the present disclosure may be used to assess the effect of a therapeutic intervention.

The methods of the present disclosure may be used for biomarker discovery. Monitoring proteome expression in subjects with and without disease may identify biomarkers. Monitoring proteome expression in subjects prior to developing diseases, or in subjects at risk of developing diseases may identify biomarkers that predict risk. Evaluating the proteome expression of a subject may indicate the health of the subject or the risk of developing certain diseases or disorders. The methods of this disclosure may be used to evaluate therapies, or differentiate drug/therapy responders from non-responders. The methods of this disclosure may be of particular use for personalized medicine.

The methods of the present disclosure may be used to diagnose disease. Different diseases or disease stages may be associated with different panels of protein expression. Different panels of protein expression may be associated with different treatment outcomes for each given treatment. A subject's proteome expression data may be used to diagnose the subject and/or select the most appropriate therapy.

The methods of the present disclosure may be used to identify the individual or species a sample come from. For example the methods of the present disclosure could be used to determine if a sample is actually from the claimed species or source. The methods described herein may have an advantage over PCR based methods in samples with abundant protein but limited nucleic acid. For example identifying the origins of honey samples. For further example the methods of the present disclosure could be used to assess food safety and food quality control.

The methods of the present disclosure may be used to identify any single protein molecule from a pool of protein molecules using less affinity reagents than the number of possible proteins. For example the methods may identify, with certainty above a threshold amount, an unidentified single protein molecule from a pool of n possible proteins, using a panel of affinity reagents, wherein the number of affinity reagents in the panel is m, and wherein m is less than n. The unidentified protein may be a known protein which corresponds to known protein and gene sequences, or may be an unknown protein without known protein or gene sequences. In the case of an unknown protein this method may identify a signature of the unknown protein, and thus the presence and quantity of the unknown protein, but not the amino acid sequence. The methods of the present disclosure may be used to select a panel of m affinity reagents capable of identifying an unidentified protein selected from a pool of n possible proteins. The methods disclosed herein are also capable of uniquely identifying and quantifying n proteins in a mixture of proteins using m binding reagents, and wherein each protein is identified via a unique profile of binding by a subset of the m the binding reagents. Further, m may be less than about a half, a third, a fourth, a fifth, a sixth, a seventh, a tenth, a twentieth, a fiftieth or a hundredth of n. For further example the present disclosure may be used to select a panel of less than about 100, 200, 300, 400, 500, 600, 700, 800, 900, 1000, 1500, 2000, 2500, 3000, 3500, or 4000 affinity reagents, such that the panel of affinity reagents is capable of uniquely identifying each of at least about 100, 500, 1000, 2000, 3000, 4000, 5000, 6000, 7000, 8000, 9000, 10,000, 12,000, 14,000, 16,000, 18,000, 20,000, 25,000, 30,000, 35,000, 40,000, 50,000, 100,000, 200,000, 300,000, 400,000, 500,000, 600,000, 700,000, 800,000, 900,000, 1,000,000, 2,000,000, 3,000,000, 4,000,000, or 5,000,000 different proteins.

The methods of the present disclosure may be capable of identifying most of the proteins in a proteome. The methods of the present disclosure may be capable of identifying most of the proteins in a mammalian, bird, fish, amphibian, reptilian, vertebrate, invertebrate, plant, fungal, bacterial or archaeal proteome. The methods of the present disclosure may be capable of identifying more than about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% of the proteins in a proteome.

EXAMPLES

Example 1: Protein Identification Using Antibodies that Bind Unique 3-Mer Peptides A computational experiment was performed to determine the relationship between the percentage coverage of the set of all epitopes in a proteome and the percentage of the proteome that may be identified using the methods of this disclosure. For this experiment the set of all 3-mer amino acid epitopes was selected. Protein modifications were not considered. As there are 20 naturally occurring amino acids the total set of all 3-mer epitopes is 20×20×20=8000 possible epitopes. For the simulation x was set as the number of epitopes screened in an experiment, for each value of x from 1 to 8000 a set of x epitopes were randomly selected and the percentage of the proteome which could be identified was calculated. FIG. 13 shows the results of this simulation.

Figure 15:
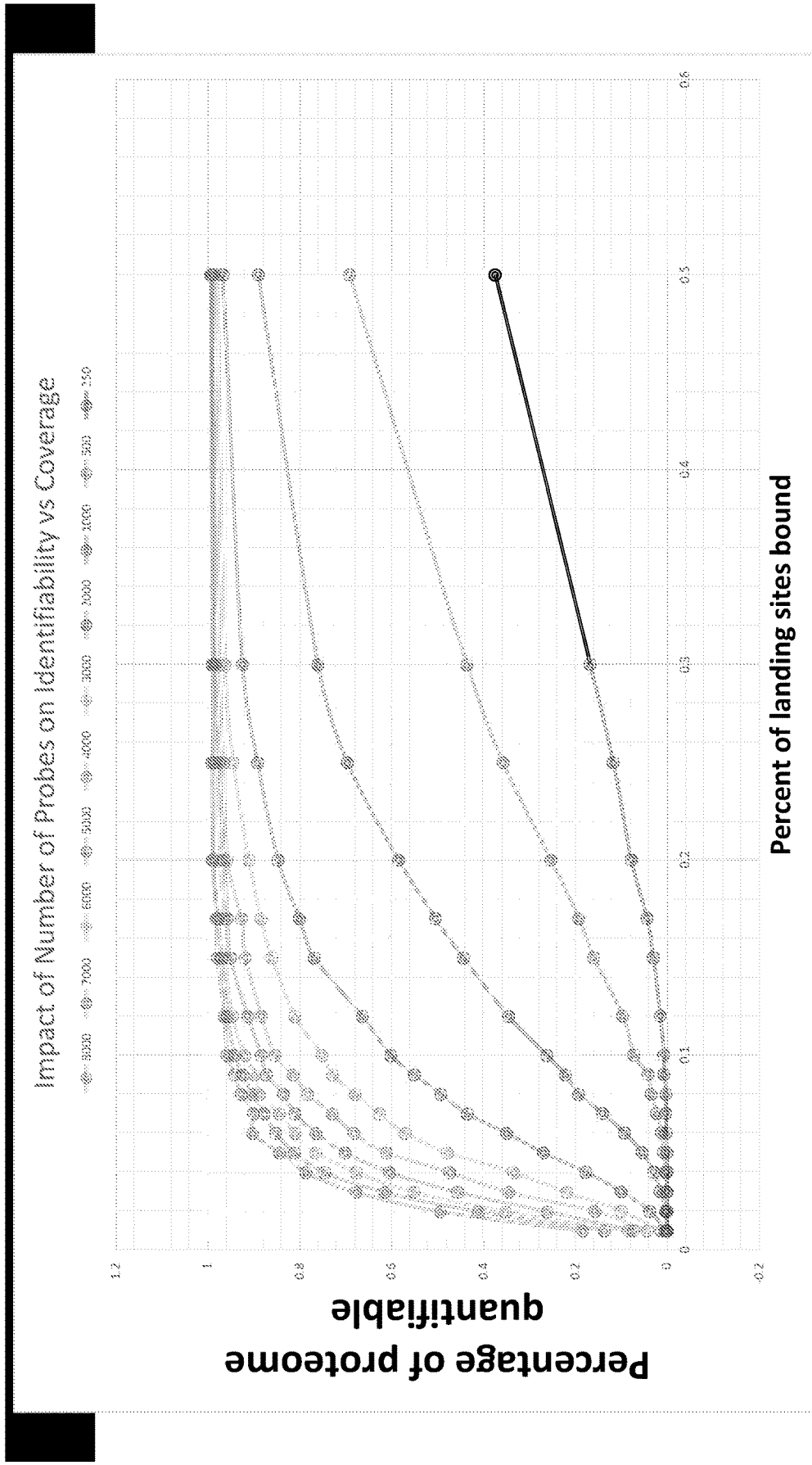
FIG. 15 illustrates an example of impact of number of 3-mer d-code probes on identifiability vs coverage of proteome, in accordance with embodiments herein.

Example 2: Protein Identification Using Antibodies that Bind Unique 3-Mer Peptides A further computational experiment was performed to determine the impact of the number of affinity reagents on identifiability and coverage. Data series were calculated for a range of affinity reagent pool sizes to show the percentage of the proteome which may be identified (y axis) for each possible coverage of a protein and the results are shown in Table 1. For example, a protein with 100 amino acids has 98 3-mer amino acid epitopes "landing sites", if 20% of these 3-mer amino acid epitopes are bound that may or may not be sufficient to identify the protein. As shown in FIG. 15, with an affinity reagent pool of 250 3-mer specific affinity reagents if 20% of the landing sites of each protein are bound, then only about 7% of the proteome may be identified. For an affinity reagent pool of 8000 affinity reagents then with 20% of landing sites bound about 98% of the proteome may be identified.

that the unknown protein is bound by the affinity reagents DGD, AEV, LAD, GDG, and QSA. Analysis of the sequences of the four proteins of this proteome indicates that only GFP contains all five of these three amino acid motifs, these motifs are underlined in the sequence of FIG. 18. Thus, it is determined that the single molecule of the unknown protein is a GFP protein.

TABLE 1

Impact of number of 3-mer d-code probes on identifiability vs coverage of proteome

|  | 8000 | 7000 | 6000 | 5000 | 4000 | 3000 | 2000 | 1000 | 500 | 250 |
|---|---|---|---|---|---|---|---|---|---|---|
| 1.00% | 0.1825 | 0.135 | 0.0845 | 0.072 | 0.042 | 0.0125 | 0.0035 | 0 | 0 | 0 |
| 2.00% | 0.492 | 0.41 | 0.3515 | 0.26 | 0.156 | 0.0985 | 0.037 | 0.0035 | 0.0005 | 0 |
| 3.00% | 0.677 | 0.614 | 0.55 | 0.455 | 0.344 | 0.2175 | 0.0985 | 0.015 | 0.0005 | 0 |
| 4.00% | 0.786 | 0.745 | 0.676 | 0.604 | 0.472 | 0.334 | 0.176 | 0.029 | 0.003 | 0 |
| 5.00% | 0.843 | 0.811 | 0.765 | 0.7005 | 0.61 | 0.4765 | 0.269 | 0.054 | 0.0075 | 0 |
| 6.00% | 0.9025 | 0.852 | 0.809 | 0.7645 | 0.6815 | 0.569 | 0.3485 | 0.092 | 0.012 | 0.0015 |
| 7.00% | 0.9005 | 0.877 | 0.8435 | 0.81 | 0.7285 | 0.626 | 0.4345 | 0.1395 | 0.022 | 0.0025 |
| 8.00% | 0.9275 | 0.9025 | 0.8875 | 0.835 | 0.782 | 0.678 | 0.491 | 0.192 | 0.034 | 0.002 |
| 9.00% | 0.9415 | 0.923 | 0.898 | 0.8725 | 0.814 | 0.728 | 0.5495 | 0.221 | 0.0415 | 0.0065 |
| 10.00% | 0.9575 | 0.941 | 0.919 | 0.8835 | 0.8535 | 0.751 | 0.601 | 0.261 | 0.0715 | 0.007 |
| 12.00% | 0.9635 | 0.957 | 0.946 | 0.913 | 0.8825 | 0.81 | 0.663 | 0.3445 | 0.0955 | 0.0145 |
| 15.00% | 0.978 | 0.969 | 0.962 | 0.9505 | 0.9185 | 0.8605 | 0.7675 | 0.443 | 0.1585 | 0.0295 |
| 17.00% | 0.981 | 0.9765 | 0.9645 | 0.9575 | 0.927 | 0.884 | 0.8005 | 0.503 | 0.1915 | 0.0435 |
| 20.00% | 0.9885 | 0.986 | 0.9725 | 0.9635 | 0.9575 | 0.9105 | 0.847 | 0.584 | 0.2525 | 0.0775 |
| 25.00% | 0.99 | 0.9865 | 0.9785 | 0.9745 | 0.966 | 0.9445 | 0.8915 | 0.6955 | 0.357 | 0.1165 |
| 30.00% | 0.9865 | 0.9895 | 0.985 | 0.9825 | 0.973 | 0.9625 | 0.9245 | 0.76 | 0.4355 | 0.1665 |
| 50.00% | 0.9915 | 0.9915 | 0.9935 | 0.9895 | 0.9855 | 0.978 | 0.967 | 0.89 | 0.691 | 0.374 |

Example 3: Illuminated Protein Molecules Conjugated on a Substrate

Figure 16A:
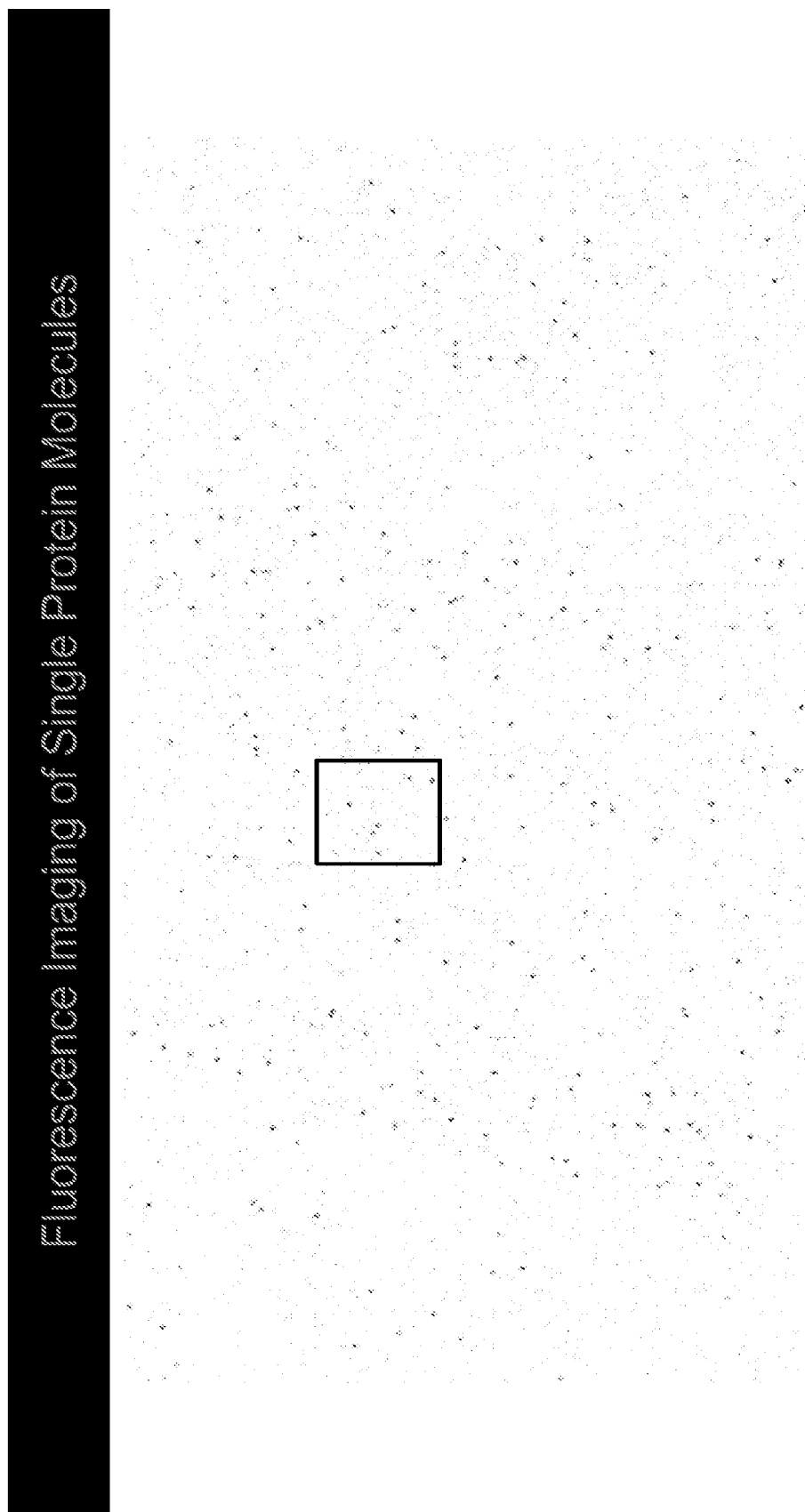
FIG. 16A illustrates an image showing single protein molecules conjugated on a substrate, in accordance with embodiments herein.
Figure 16B:
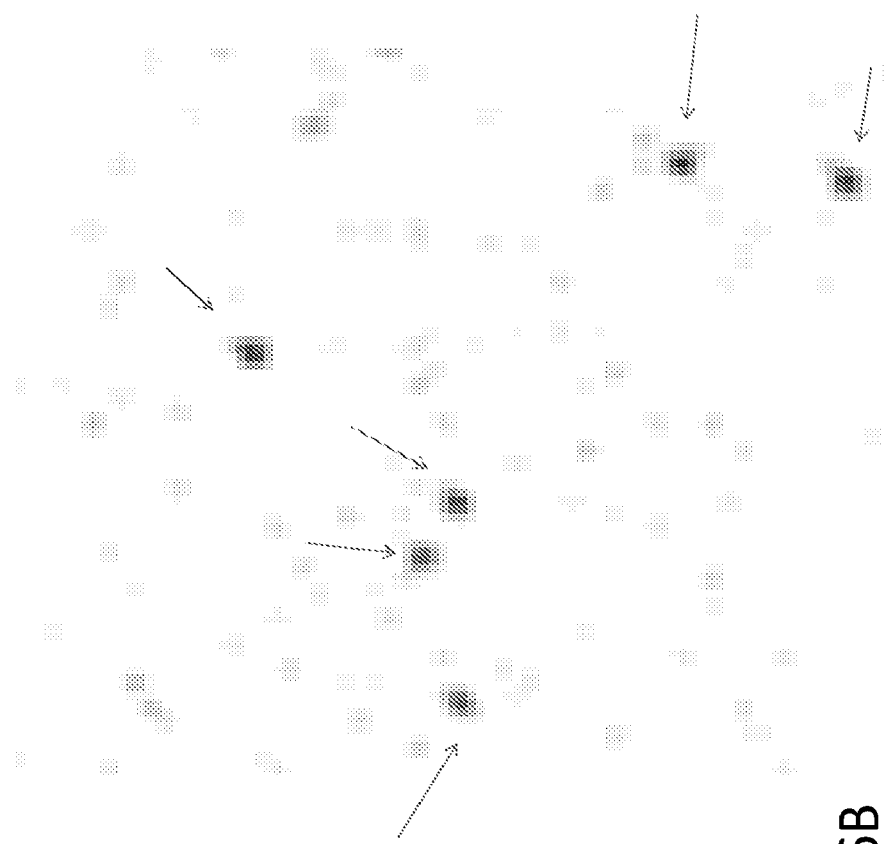
FIG. 16B illustrates an image showing a blown up portion of the indicated area of FIG. 16A with conjugated proteins indicated by arrows, in accordance with embodiments herein.

A fluorescent protein sample, Phycoerythrin, was directly conjugated to an NHS-Ester coated coverslip for 4 hours in an incubation chamber at 4 degrees. The fluorescent protein sample was then imaged on a Leica DMi8 with a Hamamatsu orca flash 4.0 camera using 300 ms exposure. FIGS. 16A and 16B show a resulting image captured (colors reversed for clarity). As seen in FIGS. 16A and 16B, each dark spot represents an area of fluorescence signal indicating the presence of a protein. FIG. 16B is a blow-up of FIG. 16A. Arrows in FIG. 16B indicate signals representing proteins that are clearly distinguishable from background noise.

Figure 17:
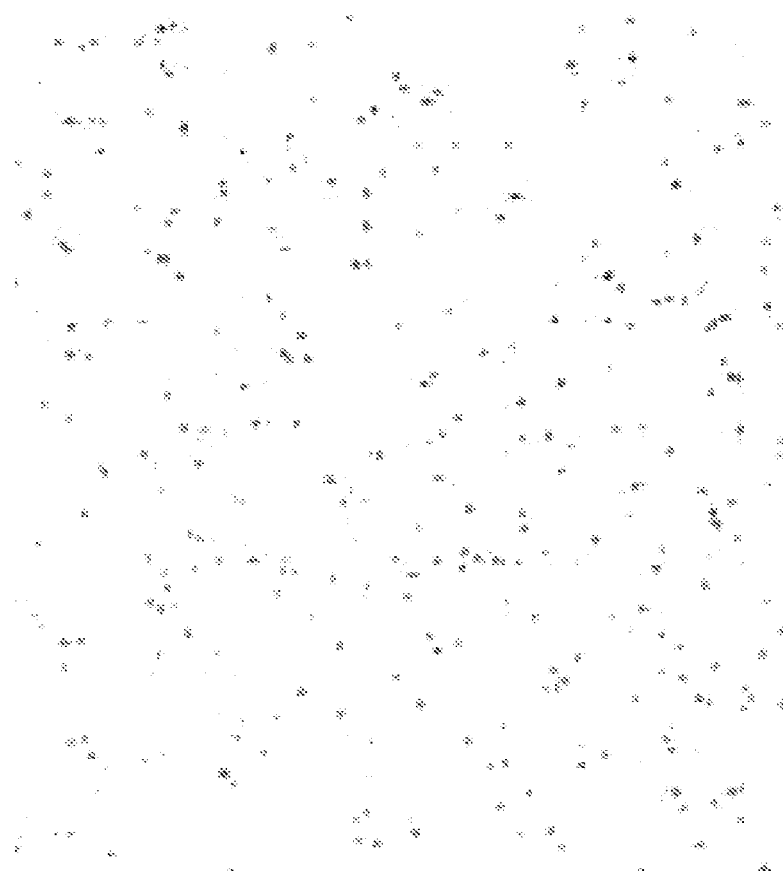
FIG. 17 illustrates identification of a protein, in accordance with embodiments herein.

A second protein sample, Green Fluorescent Protein, was denatured and directly conjugated to an NHS-Ester coated coverslip for 4 hours in an incubation chamber at 4 degrees. Initial imaging showed no baseline residual fluorescence, indicating complete denaturation of the Green Fluorescent Protein. The protein was then incubated with an anti-peptide antibody with an attached Alexa-Fluor 647. The anti-peptide antibody was then rinsed with 0.1% Tween-20. This was then imaged using TIRF on a Nikon Eclipse Ti with an Andor NEO sCMOS camera. FIG. 17 shows a resulting image captured (colors reversed for clarity).

Example 4: Identification of a Protein

Figure 14:
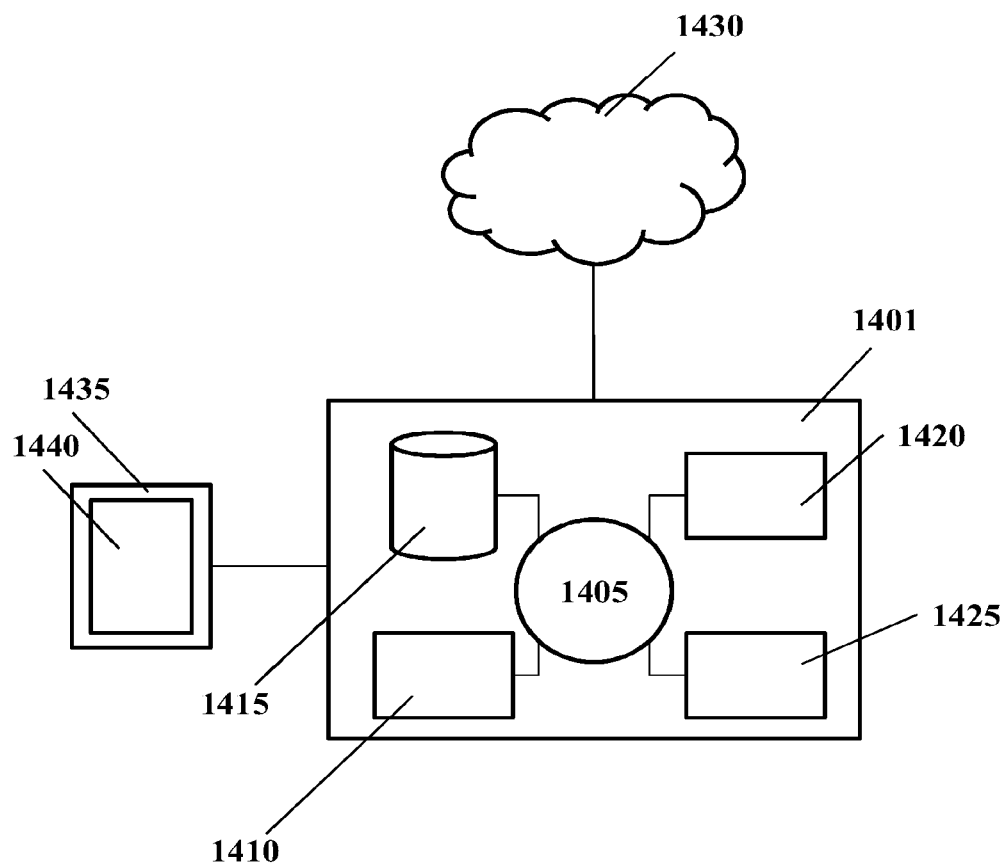
FIG. 14 illustrates a computer control system that is programmed or otherwise configured to implement methods provided herein.

A proteome of four possible proteins, Green Fluorescent Protein, RNASE1, LTF, and GSTM1, is depicted in FIG. 18. In this example, a single molecule of an unknown protein from this proteome is conjugated to a position on a substrate. The unknown protein is sequentially interrogated by a panel of nine different affinity reagents. Each of the nine different affinity reagents recognize a different amino acid trimer [AAA, AAC, AAD, AEV, GDG, QSA, LAD, TRK, DGD], and each is labeled with a fluorescent dye. It is determined Computer Control Systems The present disclosure provides computer control systems that are programmed to implement methods of the disclosure. FIG. 14 shows a computer system 1401 that is programmed or otherwise configured to characterize and identify biopolymers, such as proteins. The computer system 1401 can regulate various aspects of assessing and analyzing samples of the present disclosure, such as, for example, observing signals at unique spatial addresses of a substrate; determining a presence of an identifiable tag linked to a biopolymer portion at unique spatial addresses based on observed signals; assessing the determined identifiable tags against a database of biopolymer sequences to determine characteristics of biopolymer portions. The computer system 1401 can be an electronic device of a user or a computer system that is remotely located with respect to the electronic device. The electronic device can be a mobile electronic device.

The computer system 1401 includes a central processing unit (CPU, also "processor" and "computer processor" herein) 1405, which can be a single core or multi core processor, or a plurality of processors for parallel processing. The computer system 1401 also includes memory or memory location 1410 (e.g., random-access memory, read-only memory, flash memory), electronic storage unit 1415 (e.g., hard disk), communication interface 1420 (e.g., network adapter) for communicating with one or more other systems, and peripheral devices 1425, such as cache, other memory, data storage and/or electronic display adapters. The memory 1410, storage unit 1415, interface 1420 and peripheral devices 1425 are in communication with the CPU 1405 through a communication bus (solid lines), such as a motherboard. The storage unit 1415 can be a data storage unit (or data repository) for storing data. The computer system 1401 can be operatively coupled to a computer network ("network") 1430 with the aid of the communication interface 1420. The network 1430 can be the Internet, an internet and/or extranet, or an intranet and/or extranet that is in communication with the Internet. The network 1430 in some cases is a telecommunication and/or data network. The network 1430 can include one or more computer servers, which can enable distributed computing, such as cloud computing. The network 1430, in some cases with the aid of the computer system 1401, can implement a peer-to-peer network, which may enable devices coupled to the computer system 1401 to behave as a client or a server.

The CPU 1405 can execute a sequence of machine-readable instructions, which can be embodied in a program or software. The instructions may be stored in a memory location, such as the memory 1410. The instructions can be directed to the CPU 1405, which can subsequently program or otherwise configure the CPU 1405 to implement methods of the present disclosure. Examples of operations performed by the CPU 1405 can include fetch, decode, execute, and writeback.

The CPU 1405 can be part of a circuit, such as an integrated circuit. One or more other components of the system 1401 can be included in the circuit. In some cases, the circuit is an application specific integrated circuit (ASIC).

The storage unit 1415 can store files, such as drivers, libraries and saved programs. The storage unit 1415 can store user data, e.g., user preferences and user programs. The computer system 1401 in some cases can include one or more additional data storage units that are external to the computer system 1401, such as located on a remote server that is in communication with the computer system 1401 through an intranet or the Internet.

The computer system 1401 can communicate with one or more remote computer systems through the network 1430. For instance, the computer system 1401 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1401 via the network 1430.

Methods as described herein can be implemented by way of machine (e.g., computer processor) executable code stored on an electronic storage location of the computer system 1401, such as, for example, on the memory 1410 or electronic storage unit 1415. The machine executable or machine readable code can be provided in the form of software. During use, the code can be executed by the processor 1405. In some cases, the code can be retrieved from the storage unit 1415 and stored on the memory 1410 for ready access by the processor 1405. In some situations, the electronic storage unit 1415 can be precluded, and machine-executable instructions are stored on memory 1410.

The code can be pre-compiled and configured for use with a machine have a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semi-conductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1401 can include or be in communication with an electronic display 1435 that comprises a user interface (UI) 1440. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1405. The algorithm can, for example, determine characteristics and/or identities of biopolymer portions, such as protein portions. For example, algorithms may be used to determine a most likely identity of a candidate biopolymer portion, such as a candidate protein portion.

In some embodiments aptamers or peptamers which recognize short epitopes present in many different proteins may be referred to as digital aptamers or digital peptamers. An aspect of the invention provides a set of digital aptamers or digital peptamers, wherein the set comprises at least about 15 digital aptamers or digital peptamers, wherein each of the 15 digital aptamers or digital peptamers has been characterized to bind specifically to a different epitope consisting of 3 or 4 or 5 consecutive amino acids, and wherein each digital aptamer or digital peptamer recognizes a plurality of distinct and different proteins that comprise the same epitope to which the digital aptamer or digital peptamer binds. In some embodiments the set of digital aptamers or digital peptamers comprises 100 digital aptamers or digital peptamers that bind epitopes consisting of 3 consecutive amino acids. In some embodiments the set of digital aptamers or digital peptamers further comprises 100 digital aptamers that bind epitopes consisting of 4 consecutive amino acids. In some embodiments the set of digital aptamers or digital peptamers further comprises 100 digital aptamers or digital peptamers that bind epitopes consisting of 5 consecutive amino acids. In some cases, digital affinity reagents may be an antibody, aptamer, peptamer, peptide or Fab fragment.

In some embodiments the set of digital aptamers comprises at least about 20, 30, 40, 50, 60, 70, 80, 90, 100, 200, 300, 400, 500, 600, 700 800, 900, or 1000 digital aptamers. In some embodiments the set of digital aptamers comprises at least 1000 digital aptamers that bind epitopes consisting of 4 consecutive amino acids. In some embodiments the set of digital aptamers further comprises at least 100 digital aptamers that bind epitopes consisting of 5 consecutive amino acids. The set of digital aptamers further comprises at least 100 digital aptamers that bind epitopes consisting of 3 consecutive amino acids. In some embodiments the set of digital aptamers are immobilized on a surface. In some embodiments the surface is an array.

In another aspect the invention provides a method for generating a protein binding profile of a sample comprising a plurality of different proteins, said method comprising: contacting said sample with a set of digital aptamers, under conditions that permit binding, wherein the set of digital aptamers comprises at least about 15 digital aptamers, wherein each of the 15 digital aptamers has been characterized to bind specifically to a different epitope consisting of 3 or 4 or 5 consecutive amino acids, and each digital aptamer recognizes a plurality of distinct and different proteins that comprise the same epitope to which the digital aptamer binds; optionally removing an unbound protein; and detecting binding of protein to said digital aptamers, whereby a protein binding profile of the sample is generated.

In some embodiments the method further comprises the step of treating the sample with a protein cleaving agent prior to step (a) of contacting the sample with the set of digital aptamers under conditions that permit binding.

In another aspect the invention comprises a library of protein binding profiles for two or more different samples each of which comprises a plurality of proteins, said method comprising: contacting a sample with a set of digital aptamers under conditions that permit binding, wherein the set of digital aptamers comprises at least about 15 digital aptamers, wherein each of the 15 digital aptamers has been characterized to bind specifically to a different epitope consisting of 3 or 4 or 5 consecutive amino acids, and each digital aptamer recognizes a plurality of distinct and different proteins that comprise the same epitope to which the digital aptamer binds; optionally removing an unbound protein; generating a protein binding profile of the sample being tested by detecting binding of protein to the digital aptamers, whereby a protein binding profile is generated; and repeating the steps above with at least two samples.

In some embodiments the method further comprises the step of treating the sample with a protein cleaving agent prior to the step of contacting the sample with the set of digital aptamers under conditions that permit binding.

In another aspect the invention comprises a method for characterizing a test sample, comprising: contacting the test sample with a set of digital aptamers under conditions that permit binding, wherein the set of digital aptamers comprises at least about 15 digital aptamers, wherein each of the 15 digital aptamers has been characterized to bind specifically to a different epitope consisting of 3 or 4 or 5 consecutive amino acids, and each digital aptamer recognizes a plurality of distinct and different proteins that comprise the same epitope to which the digital aptamer binds; optionally removing an unbound protein generating a protein binding profile of said test sample by detecting binding of protein to the digital aptamers; and comparing the generated protein binding profile of the test sample with a protein binding profile of a reference sample to characterize the test sample.

In another aspect the invention comprises a method for determining presence or absence of a bacteria, virus, or cell in a test sample, said method comprising: contacting the test sample with a set of digital aptamers under conditions that permit binding, wherein the set of digital aptamers comprises at least about 15 digital aptamers, wherein each of the 15 digital aptamers has been characterized to bind specifically to a different epitope consisting of 3 or 4 or 5 consecutive amino acids, and each digital aptamer recognizes a plurality of distinct and different proteins that comprise the same epitope to which the digital aptamer binds; optionally removing an unbound protein; generating a protein binding profile of the test sample by detecting binding of protein to the digital aptamers, whereby a protein binding profile is generated; and comparing the protein binding profile of the test sample with a protein binding profile of a reference sample, whereby presence or absence of the bacteria, virus or cell in the test sample is determined by the comparison.

In another aspect the invention comprises a method for identifying a test protein in a sample, said method comprising: contacting a sample comprising or suspected of comprising the test protein with a set of digital aptamers that comprises at least about 15 digital aptamers, wherein each of the 15 digital aptamers has been characterized to bind specifically to a different epitope consisting of 3 or 4 or 5 consecutive amino acids, and each digital aptamer recognizes a plurality of distinct and different proteins that comprise the same epitope to which the digital aptamer binds; and determining the identity of the test protein by detecting of binding of the test protein to the set of digital aptamers, wherein at least about six digital aptamers bind the test protein; and wherein presence of binding indicates presence of at least about six epitopes in the test protein, wherein the identity of the at least about six epitopes is used to identify the test protein.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

Notwithstanding the appended claims, the disclosure set forth herein is also defined by the following clauses:

1. A set of digital aptamers, wherein the set comprises at least about 15 digital aptamers, wherein each of the 15 digital aptamers has been characterized to bind specifically to a different epitope consisting of 3 or 4 or 5 consecutive amino acids, and wherein each digital aptamer recognizes a plurality of distinct and different proteins that comprise the same epitope to which the digital aptamer binds.

2. The set of digital aptamers according to clause 1, wherein the set comprises 100 digital aptamers that bind epitopes consisting of 3 consecutive amino acids.

3. The set of digital aptamers according to clause 1, wherein the set further comprises 100 digital aptamers that bind epitopes consisting of 4 consecutive amino acids.

4. The set of digital aptamers according to clause 3, wherein the set further comprises 100 digital aptamers that bind epitopes consisting of 5 consecutive amino acids.

5. The set of digital aptamers according to clause 1, wherein the set comprises at least about 20, 30, 40, 50, 60, 70, 80, 90, 100, 200, 300, 400, 500, 600, 700 800, 900, or 1000 digital aptamers.

6. The set of digital aptamers according to clause 1, wherein the set comprises at least 1000 digital aptamers that bind epitopes consisting of 4 consecutive amino acids.

7. The set of digital aptamers according to clause 6, wherein the set further comprises at least 100 digital aptamers that bind epitopes consisting of 5 consecutive amino acids.

8. The set of digital aptamers according to clause 7, wherein the set further comprises at least 100 digital aptamers that bind epitopes consisting of 3 consecutive amino acids.

9. The set of digital aptamers according to any of clauses 1-8, wherein the digital aptamers are immobilized on a surface.

10. The set of digital aptamers according to clause 9, wherein the surface is an array.

11. A method for generating a protein binding profile of a sample comprising a plurality of different proteins, said method comprising:
a) contacting said sample with a set of digital aptamers, under conditions that permit binding, wherein the set of digital aptamers comprises at least about 15 digital aptamers, wherein each of the 15 digital aptamers has been characterized to bind specifically to a different epitope consisting of 3 or 4 or 5 consecutive amino acids, and each digital aptamer recognizes a plurality of distinct and different proteins that comprise the same epitope to which the digital aptamer binds;
b) optionally removing an unbound protein; and
c) detecting binding of protein to said digital aptamers, whereby a protein binding profile of the sample is generated.

12. The method of clause 11, wherein the method further comprises the step of treating the sample with a protein cleaving agent prior to step (a) of contacting the sample with the set of digital aptamers under conditions that permit binding.

13. A method for generating a library of protein binding profiles for two or more different samples each of which comprises a plurality of proteins, said method comprising:
a) contacting a sample with a set of digital aptamers under conditions that permit binding, wherein the set of digital aptamers comprises at least about 15 digital aptamers, wherein each of the 15 digital aptamers has been characterized to bind specifically to a different epitope consisting of 3 or 4 or 5 consecutive amino acids, and each digital aptamer recognizes a plurality of distinct and different proteins that comprise the same epitope to which the digital aptamer binds;
b) optionally removing an unbound protein;
c) generating a protein binding profile of the sample being tested by detecting binding of protein to the digital aptamers, whereby a protein binding profile is generated; and
d) repeating steps (a) through (c) with at least two samples.

14. The method of clause 13, wherein the method further comprises the step of treating the sample with a protein cleaving agent prior to step (a) of contacting the sample with the set of digital aptamers under conditions that permit binding.

15. A library of protein binding profiles, wherein the library is prepared using the method of clause 13.

16. A method for characterizing a test sample, comprising:
a) contacting the test sample with a set of digital aptamers under conditions that permit binding, wherein the set of digital aptamers comprises at least about 15 digital aptamers, wherein each of the 15 digital aptamers has been characterized to bind specifically to a different epitope consisting of 3 or 4 or 5 consecutive amino acids, and each digital aptamer recognizes a plurality of distinct and different proteins that comprise the same epitope to which the digital aptamer binds;
b) optionally removing an unbound protein;
c) generating a protein binding profile of said test sample by detecting binding of protein to the digital aptamers; and
d) comparing the generated protein binding profile of the test sample with a protein binding profile of a reference sample to characterize the test sample.

17. A method for determining presence or absence of a bacteria, virus, or cell in a test sample, said method comprising
a) contacting the test sample with a set of digital aptamers under conditions that permit binding, wherein the set of digital aptamers comprises at least about 15 digital aptamers, wherein each of the 15 digital aptamers has been characterized to bind specifically to a different epitope consisting of 3 or 4 or 5 consecutive amino acids, and each digital aptamer recognizes a plurality of distinct and different proteins that comprise the same epitope to which the digital aptamer binds;
b) optionally removing an unbound protein;
c) generating a protein binding profile of the test sample by detecting binding of protein to the digital aptamers, whereby a protein binding profile is generated; and
d) comparing the protein binding profile of the test sample with a protein binding profile of a reference sample, whereby presence or absence of the bacteria, virus or cell in the test sample is determined by the comparison.

18. A method for identifying a test protein in a sample, said method comprising
a) contacting a sample comprising or suspected of comprising the test protein with a set of digital aptamers that comprises at least about 15 digital aptamers, wherein each of the 15 digital aptamers has been characterized to bind specifically to a different epitope consisting of 3 or 4 or 5 consecutive amino acids, and each digital aptamer recognizes a plurality of distinct and different proteins that comprise the same epitope to which the digital aptamer binds; and
b) determining the identity of the test protein by detecting of binding of the test protein to the set of digital aptamers, wherein at least about six digital aptamers bind the test protein; and wherein presence of binding indicates presence of at least about six epitopes in the test protein, wherein the identity of the at least about six epitopes is used to identify the test protein.

19. A method of determining protein characteristics, the method comprising:
obtaining a substrate in which portions of one or more proteins are conjugated to the substrate such that each individual (at the molecular level) protein portion has a unique, optically resolvable, spatial address;
applying a fluid containing a first through (ordered) nth set of one or more affinity reagents to the substrate, wherein each of the one or more affinity reagents is specific to one epitope (contiguous or non-contiguous amino acid sequence) of a portion of the one or more proteins, and wherein each affinity reagent of the first through nth set of one or more of affinity reagents is linked to an identifiable tag;
after each application to the substrate of the first and subsequent through nth set of one or more of affinity reagents, performing the following steps:
observing the identifiable tag;
identifying one or more unique spatial addresses of the substrate having one or more observed signal;
determining that each portion of the one or more proteins having an identified unique spatial address contains the one or more epitopes associated with the one or more observed signals; and
determining the characteristics of each protein portion based on the one or more epitopes.

20. A method of determining protein characteristics, the method comprising:
obtaining a substrate in which portions of one or more proteins are conjugated to the substrate such that the substrate has a plurality of locations, each location comprising either a single protein, or a pool of proteins of which at least 60% of the proteins share the same amino acid sequence;
applying a fluid containing a first through (ordered) nth set of one or more affinity reagents to the substrate, wherein each of the one or more affinity reagents is specific to one epitope (contiguous or non-contiguous amino acid sequence) of a portion of the one or more proteins, and wherein each affinity reagent of the first through nth set of one or more of affinity reagents is linked to an identifiable tag;
after each application to the substrate of the first and subsequent through nth set of one or more of affinity reagents, performing the following steps:
observing the identifiable tag;
identifying one or more unique spatial addresses of the substrate having one or more observed signal;
determining that each portion of the one or more proteins having an identified unique spatial address contains the one or more epitopes associated with the one or more observed signals; and
determining the characteristics of each protein portion based on the one or more epitopes.

21. The method of clause 19 or 20, wherein the method may be used to identify at least 400 different proteins at least 10% more quickly than techniques for protein identification that rely upon data from a mass spectrometer 22. The method of clause 21, wherein the method identifies the at least 400 different proteins with at least 50% accuracy.

23. The method of clause 22, wherein the method identifies a particular protein as a member of a particular family of proteins independent of whether the method identifies the particular protein itself within a threshold degree of confidence of more than 10%.

24. The method of clause 19 or 20, wherein the portions of one or more proteins are separated on the substrate based on the size of the protein.

25. The method of clause 19 or 20, wherein the portions of one or more proteins are separated on the substrate based on the charge of the protein.

26. The method of clause 19 or 20, wherein the substrate comprises microwells.

27. The method of clause 19 or 20, wherein the substrate comprises microwells of different sizes.

28. The method of clause 19 or 20, wherein the proteins are attached to the substrate via a biotin attachment.

29. The method of clause 19 or 20, wherein the proteins are attached to the substrate via a nucleic acid.

30. The method of clause 29, wherein the proteins are attached to the substrate via a nucleic acid nanoball.

31. The method of clause 19 or 20, wherein the proteins are attached to the substrate via a nanobead.

32. The method of clause 19 or 20, wherein obtaining the substrate in which portions of one or more proteins are bound comprises obtaining a substrate with an ordered array of functional groups and applying a protein sample such that each functional group conjugates to no more than one protein molecule from the sample.

33. The method of clause 32, wherein obtaining a substrate with an ordered array of functional groups comprises using a method selected from the group consisting of photolithography, Dip-Pen nanolithography, nanoimprint lithography, nanosphere lithography, thermal scanning probe lithography, local oxidation nanolithography, molecular self-assembly, stencil lithography, and electron-beam lithography.

34. The method of clause 32, wherein each functional group is located at least about 300 nm apart from each other functional group.

35. The method of clause 19 or 20, wherein the substrate comprises an ordered array of microwells of different sizes.

36. The method of clause 19 or 20, wherein obtaining the substrate comprises conjugating a first sample of proteins to the substrate, using a protein dye to detect each location with a bound protein from the first sample, conjugating a second sample, and using a protein dye to detect each location with a bound protein from the second sample.

37. The method of clause 19 or 20, wherein obtaining the substrate comprises conjugating a first sample of proteins to the substrate, using a protein dye to detect each location with a bound protein from the first sample, determining from the number of bound proteins the fraction of functional groups on the substrate which are not bound by a protein.

38. The method of clause 19 or 20, wherein an affinity reagent may comprise a pool of components which bind the same core sequence with different flanking sequences, such that at least one component has a binding affinity above a threshold for binding any instance of the core sequence regardless of flanking sequence.

What is claimed is:

1. A flowcell, comprising:
   at least a first surface on a substrate disposed within the flowcell;
   a plurality of polypeptide molecules from a biological sample immobilized on the at least first surface, wherein the at least first surface comprises at least 1,000,000 individual polypeptide molecules immobilized on the at least first surface, each of the at least 1,000,000 individual polypeptide molecules being positioned to be individually spatially resolvable from each other individual polypeptide on the first surface;
   wherein the plurality of polypeptide molecules immobilized on the first surface comprises a plurality of different polypeptides present on the first surface, and wherein the number of first polypeptides immobilized on the surface corresponds to the level of the first polypeptides in the biological sample; and wherein the polypeptide molecules are attached to the first surface of the substrate through a nucleic acid attachment.

2. The flowcell of claim 1, wherein the plurality of different polypeptide molecules comprises at least 100 different polypeptides.

3. The flowcell of claim 2, wherein the plurality of different polypeptide molecules comprises at least 1,000 different polypeptides.

4. The flowcell of claim 3, wherein the plurality of different polypeptide molecules comprises at least 10,000 different polypeptides.

5. The flowcell of claim 3, wherein the plurality of different polypeptide molecules comprises at least 20,000 different polypeptides.

6. The flowcell of claim 4, wherein the plurality of different polypeptides comprises at least 50,000 different polypeptides.

7. The flowcell of claim 5, wherein the plurality of different polypeptides comprises at least 100,000 different polypeptides.

8. The flowcell of claim 1, further comprising at least 10,000,000 individual polypeptide molecules immobilized on the first surface, each of the at least 10,000,000 individual polypeptide molecules being positioned to be individually spatially resolvable from each other individual polypeptide on the first surface.

9. The flowcell of claim 1, further comprising at least 100,000,000 individual polypeptide molecules immobilized on the first surface, each of the at least 100,000,000 individual polypeptide molecules being positioned to be individually spatially resolved resolvable from each other individual polypeptide on the first surface.

10. The flowcell of claim 1, further comprising at least 1,000,000,000 individual polypeptide molecules immobilized on the first surface, each of the at least 1,000,000,000 individual polypeptide molecules being positioned to be individually spatially resolvable from each other individual polypeptide on the first surface.

11. The flowcell of claim 1, further comprising at least 100,000,000,000 individual polypeptide molecules immobilized on the first surface, each of the at least 100,000,000,000 individual polypeptide molecules being positioned to be individually addressable/spatially resolved/optically resolvable from each other individual polypeptide on the first surface.

12. The flow cell of claim 1, further comprising a source of a plurality of different affinity reagents fluidly connected to the flowcell, each of the plurality of different affinity reagents having a specificity for one or more epitopes in the plurality of individual polypeptide molecules immobilized on the first surface, such that a binding profile of the plurality of different affinity reagents against the polypeptides immobilized on the first surface is capable of characterizing at least 90% of the plurality of different polypeptides immobilized on the first surface.

13. The flowcell of claim 1, wherein the plurality of polypeptide molecules immobilized on the first surface comprise intact proteins.

14. The flowcell of claim 11, wherein the plurality of polypeptide molecules immobilized on the first surface are denatured.

15. The flowcell of claim 1, wherein the polypeptide molecules are from a subject suspected of having a disease or disorder.

16. The flowcell of claim 1, wherein the polypeptide molecules are from an embryo, fetus, or pregnant woman.

17. The flowcell of claim 1, wherein the polypeptide molecules were treated to remove proteins over 400kD.

18. The flowcell of claim 1, wherein the substrate comprises a functionalized substrate with chemical links to the polypeptide molecules.

19. The flowcell of claim 1, wherein the nucleic acid attachment comprises an oligonucleotide attachment.

20. The flowcell of claim 19, wherein the nucleic acid attachment comprises a nucleic acid nanoball attachment.

21. The flowcell of claim 1, wherein the flow cell comprises a textured substrate and microwells.

22. The flowcell of claim 1, wherein the substrate comprises a silane treated substrate.

23. The flowcell of claim 22, wherein the silane treated substrate comprises an epoxysilane, acrylatesilane or acrylamidesilane treated substrate.

24. The flowcell of claim 1, wherein the flow cell comprises openings for channels at the bottom of the flow cell.

* * * * *

UNITED STATES PATENT AND TRADEMARK OFFICE
CERTIFICATE OF CORRECTION

PATENT NO. : 11,448,647 B2
APPLICATION NO. : 17/534405
DATED : September 20, 2022
INVENTOR(S) : Parag Mallick It is certified that error appears in the above-identified patent and that said Letters Patent is hereby corrected as shown below:

On the Title Page

Column 2 (item (56) Other Publications), Line 1, delete "3-" and insert -- (3- --.

Page 2, Column 2 (item (56) Other Publications), Line 54, delete "HPV16oncoproteins" and insert -- HPV16 oncoproteins --.

Page 3, Column 2 (item (56) Other Publications), Line 5, delete "NEWBIOTECHNOLOGY," and insert -- NEW BIOTECHNOLOGY, --.

In the Specification

Column 7, Line 20, delete "substrate" and insert -- substrate. --.

Column 8, Line 46, delete "archael," and insert -- archaeal, --.

Column 10, Line 8, delete "ProteinaseK" and insert -- Proteinase K --.

Column 10, Line 22, delete "acis," and insert -- acids, --.

Column 11, Line 5, delete "Allophcocyanin," and insert -- Allophycocyanin, --.

Column 13, Line 11, (approx.), delete "µm" and insert -- µm. --.

Column 13, Line 16, (approx.), delete "100" and insert -- 100 µm. --.

Column 14, Line 9, delete "boro silicate" and insert -- borosilicate --.

Column 16, Line 53, delete "fluorphores" and insert -- fluorophores --.

Signed and Sealed this
Seventh Day of March, 2023

*Katherine Kelly Vidal*
Katherine Kelly Vidal
*Director of the United States Patent and Trademark Office*

Column 18, Line 61, delete "flurophores" and insert -- fluorophores --.

Column 20, Line 18, delete "$10^{-5}$M," and insert -- $10^{-5}$ M, --.

Column 20, Line 19, delete "10-M," and insert -- $10^{-7}$ M, --.

Column 20, Line 19, delete "$10^{-8}$M," and insert -- $10^{-8}$ M, --.

Column 20, Line 21, delete "$10^{-9}$M," and insert -- $10^{-9}$ M, --.

Column 20, Line 21, delete "$10^{-7}$M," and insert -- $10^{-7}$ M, --.

Column 20, Line 22, delete "$10^{-5}$M," and insert -- $10^{-5}$ M, --.

Column 20, Line 25, delete "ubiquinated" and insert -- ubiquitinated --.

Column 29, Line 55, delete "processer" and insert -- processor --.

Column 36, Line 10, delete "spectrometer" and insert -- spectrometer. --.

In the Claims

Column 49, Line 32, Claim 9, before "resolvable" delete "resolved".

Column 50, Line 26, Claim 17, delete "400kD." and insert -- 400 kD. --.

```
                       SEQUENCE LISTING

<160> NUMBER OF SEQ ID NOS: 15

<210> SEQ ID NO 1
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Lys Leu Thr Leu Lys Asn Leu Ser Met Ala Ile Met Met Ser Ile
1               5                   10                  15

Val Met Gly Ser Ser Ala Met Ala Ala Asp Ser Asn Glu Lys
            20                  25                  30

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Tyr Leu Pro Glu His Thr Leu
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Asp Tyr Leu Glu Gln Asp
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Tyr Pro Gly Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu His Asp His Tyr Leu Asp
1               5
```

```
<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Arg Ala Arg Lys Asp Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Phe Glu Glu Glu
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Glu Ile Lys Ser Leu Lys Phe
1               5

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Thr Tyr Pro Gly Arg Phe Pro Met Gly
1               5                   10

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

His Thr Phe Glu Glu Glu Ile Glu Phe Val Gln Gly Leu Asn His Ser
1               5                   10                  15

Thr Gly

<210> SEQ ID NO 11
<211> LENGTH: 40
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 11

Asn Ile Gly Ile Tyr Pro Glu Ile Lys Ala Pro Trp Phe His Gln Glu
1               5                   10                  15

Gly Lys Asp Ile Ala Ala Lys Thr Leu Glu Val Leu Lys Lys Tyr Gly
            20                  25                  30

Tyr Thr Gly Lys Asp Asp Lys Val
        35                  40

<210> SEQ ID NO 12
<211> LENGTH: 244
<212> TYPE: PRT
<213> ORGANISM: Aequorea victoria

<400> SEQUENCE: 12

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys His His
225                 230                 235                 240

His His His His

<210> SEQ ID NO 13
<211> LENGTH: 150
<212> TYPE: PRT
<213> ORGANISM: Bos taurus

<400> SEQUENCE: 13

Met Ala Leu Lys Ser Leu Val Leu Leu Ser Leu Leu Val Leu Val Leu
1               5                   10                  15

```
Leu Leu Val Arg Val Gln Pro Ser Leu Gly Lys Glu Thr Ala Ala Ala
             20                  25                  30

Lys Phe Glu Arg Gln His Met Asp Ser Ser Thr Ser Ala Ala Ser Ser
         35                  40                  45

Ser Asn Tyr Cys Asn Gln Met Met Lys Ser Arg Asn Leu Thr Lys Asp
 50                  55                  60

Arg Cys Lys Pro Val Asn Thr Phe Val His Glu Ser Leu Ala Asp Val
 65                  70                  75                  80

Gln Ala Val Cys Ser Gln Lys Asn Val Ala Cys Lys Asn Gly Gln Thr
                 85                  90                  95

Asn Cys Tyr Gln Ser Tyr Ser Thr Met Ser Ile Thr Asp Cys Arg Glu
            100                 105                 110

Thr Gly Ser Ser Lys Tyr Pro Asn Cys Ala Tyr Lys Thr Thr Gln Ala
        115                 120                 125

Asn Lys His Ile Ile Val Ala Cys Glu Gly Asn Pro Tyr Val Pro Val
    130                 135                 140

His Phe Asp Ala Ser Val
145             150

<210> SEQ ID NO 14
<211> LENGTH: 710
<212> TYPE: PRT
<213> ORGANISM: Homo sapiens

<400> SEQUENCE: 14

Met Lys Leu Val Phe Leu Val Leu Leu Phe Leu Gly Ala Leu Gly Leu
 1               5                  10                  15

Cys Leu Ala Gly Arg Arg Arg Ser Val Gln Trp Cys Ala Val Ser Gln
             20                  25                  30

Pro Glu Ala Thr Lys Cys Phe Gln Trp Gln Arg Asn Met Arg Lys Val
         35                  40                  45

Arg Gly Pro Pro Val Ser Cys Ile Lys Arg Asp Ser Pro Ile Gln Cys
 50                  55                  60

Ile Gln Ala Ile Ala Glu Asn Arg Ala Asp Ala Val Thr Leu Asp Gly
 65                  70                  75                  80

Gly Phe Ile Tyr Glu Ala Gly Leu Ala Pro Tyr Lys Leu Arg Pro Val
                 85                  90                  95

Ala Ala Glu Val Tyr Gly Thr Glu Arg Gln Pro Arg Thr His Tyr Tyr
            100                 105                 110

Ala Val Ala Val Val Lys Lys Gly Gly Ser Phe Gln Leu Asn Glu Leu
        115                 120                 125

Gln Gly Leu Lys Ser Cys His Thr Gly Leu Arg Arg Thr Ala Gly Trp
    130                 135                 140

Asn Val Pro Ile Gly Thr Leu Arg Pro Phe Leu Asn Trp Thr Gly Pro
145                 150                 155                 160

Pro Glu Pro Ile Glu Ala Ala Val Ala Arg Phe Phe Ser Ala Ser Cys
                165                 170                 175

Val Pro Gly Ala Asp Lys Gly Gln Phe Pro Asn Leu Cys Arg Leu Cys
            180                 185                 190

Ala Gly Thr Gly Glu Asn Lys Cys Ala Phe Ser Ser Gln Glu Pro Tyr
        195                 200                 205

Phe Ser Tyr Ser Gly Ala Phe Lys Cys Leu Arg Asp Gly Ala Gly Asp
    210                 215                 220

Val Ala Phe Ile Arg Glu Ser Thr Val Phe Glu Asp Leu Ser Asp Glu
```

-continued

```
                225                 230                 235                 240
Ala Glu Arg Asp Glu Tyr Glu Leu Leu Cys Pro Asp Asn Thr Arg Lys
                    245                 250                 255

Pro Val Asp Lys Phe Lys Asp Cys His Leu Ala Arg Val Pro Ser His
                260                 265                 270

Ala Val Val Ala Arg Ser Val Asn Gly Lys Glu Asp Ala Ile Trp Asn
                275                 280                 285

Leu Leu Arg Gln Ala Gln Glu Lys Phe Gly Lys Asp Lys Ser Pro Lys
            290                 295                 300

Phe Gln Leu Phe Gly Ser Pro Ser Gly Gln Lys Asp Leu Leu Phe Lys
305                 310                 315                 320

Asp Ser Ala Ile Gly Phe Ser Arg Val Pro Pro Arg Ile Asp Ser Gly
                        325                 330                 335

Leu Tyr Leu Gly Ser Gly Tyr Phe Thr Ala Ile Gln Asn Leu Arg Lys
                    340                 345                 350

Ser Glu Glu Glu Val Ala Ala Arg Arg Ala Arg Val Val Trp Cys Ala
                355                 360                 365

Val Gly Glu Gln Glu Leu Arg Lys Cys Asn Gln Trp Ser Gly Leu Ser
    370                 375                 380

Glu Gly Ser Val Thr Cys Ser Ser Ala Ser Thr Thr Glu Asp Cys Ile
385                 390                 395                 400

Ala Leu Val Leu Lys Gly Glu Ala Asp Ala Met Ser Leu Asp Gly Gly
                    405                 410                 415

Tyr Val Tyr Thr Ala Gly Lys Cys Gly Leu Val Pro Val Leu Ala Glu
                420                 425                 430

Asn Tyr Lys Ser Gln Gln Ser Ser Asp Pro Asp Pro Asn Cys Val Asp
            435                 440                 445

Arg Pro Val Glu Gly Tyr Leu Ala Val Ala Val Val Arg Arg Ser Asp
    450                 455                 460

Thr Ser Leu Thr Trp Asn Ser Val Lys Gly Lys Lys Ser Cys His Thr
465                 470                 475                 480

Ala Val Asp Arg Thr Ala Gly Trp Asn Ile Pro Met Gly Leu Leu Phe
                    485                 490                 495

Asn Gln Thr Gly Ser Cys Lys Phe Asp Glu Tyr Phe Ser Gln Ser Cys
                500                 505                 510

Ala Pro Gly Ser Asp Pro Arg Ser Asn Leu Cys Ala Leu Cys Ile Gly
            515                 520                 525

Asp Glu Gln Gly Glu Asn Lys Cys Val Pro Asn Ser Asn Glu Arg Tyr
    530                 535                 540

Tyr Gly Tyr Thr Gly Ala Phe Arg Cys Leu Ala Glu Asn Ala Gly Asp
545                 550                 555                 560

Val Ala Phe Val Lys Asp Val Thr Val Leu Gln Asn Thr Asp Gly Asn
                    565                 570                 575

Asn Asn Glu Ala Trp Ala Lys Asp Leu Lys Leu Ala Asp Phe Ala Leu
                580                 585                 590

Leu Cys Leu Asp Gly Lys Arg Lys Pro Val Thr Glu Ala Arg Ser Cys
            595                 600                 605

His Leu Ala Met Ala Pro Asn His Ala Val Val Ser Arg Met Asp Lys
    610                 615                 620

Val Glu Arg Leu Lys Gln Val Leu Leu His Gln Gln Ala Lys Phe Gly
625                 630                 635                 640

Arg Asn Gly Ser Asp Cys Pro Asp Lys Phe Cys Leu Phe Gln Ser Glu
                    645                 650                 655
```

-continued

```
Thr Lys Asn Leu Leu Phe Asn Asp Asn Thr Glu Cys Leu Ala Arg Leu
        660                 665                 670

His Gly Lys Thr Thr Tyr Glu Lys Tyr Leu Gly Pro Gln Tyr Val Ala
        675                 680                 685

Gly Ile Thr Asn Leu Lys Lys Cys Ser Thr Ser Pro Leu Leu Glu Ala
690                 695                 700

Cys Glu Phe Leu Arg Lys
705                 710

<210> SEQ ID NO 15
<211> LENGTH: 243
<212> TYPE: PRT
<213> ORGANISM: Schistosoma japonicum

<400> SEQUENCE: 15

Ser Thr Met Ser Pro Ile Leu Gly Tyr Trp Lys Ile Lys Gly Leu Val
1               5                   10                  15

Gln Pro Thr Arg Leu Leu Leu Glu Tyr Leu Glu Glu Lys Tyr Glu Glu
                20                  25                  30

His Leu Tyr Glu Arg Asp Glu Gly Asp Lys Trp Arg Asn Lys Lys Phe
            35                  40                  45

Glu Leu Gly Leu Glu Phe Pro Asn Leu Pro Tyr Tyr Ile Asp Gly Asp
    50                  55                  60

Val Lys Leu Thr Gln Ser Met Ala Ile Ile Arg Tyr Ile Ala Asp Lys
65                  70                  75                  80

His Asn Met Leu Gly Gly Cys Pro Lys Glu Arg Ala Glu Ile Ser Met
                85                  90                  95

Leu Glu Gly Ala Val Leu Asp Ile Arg Tyr Cys Val Ser Arg Ile Ala
            100                 105                 110

Tyr Ser Lys Asp Phe Glu Thr Leu Lys Val Asp Phe Leu Ser Lys Leu
        115                 120                 125

Pro Glu Met Leu Lys Met Phe Glu Asp Arg Leu Cys His Lys Thr Tyr
    130                 135                 140

Leu Asn Gly Asp His Val Thr His Pro Asp Phe Met Leu Tyr Asp Ala
145                 150                 155                 160

Leu Asp Val Val Leu Tyr Met Asp Pro Met Cys Leu Asp Ala Phe Pro
                165                 170                 175

Lys Leu Val Cys Phe Lys Lys Arg Ile Glu Ala Ile Pro Gln Ile Asp
            180                 185                 190

Lys Tyr Leu Lys Ser Ser Lys Tyr Ile Ala Trp Pro Leu Gln Gly Trp
        195                 200                 205

Gln Ala Thr Phe Gly Gly Gly Asp His Pro Pro Lys Ser Asp Leu Val
    210                 215                 220

Pro Arg Gly Ser Pro Leu Glu Val Leu Phe Gln Gly Pro Cys Gly Ser
225                 230                 235                 240

Tyr Gly Ser
```